US011944376B2

(12) United States Patent
van der Weide et al.

(10) Patent No.: US 11,944,376 B2
(45) Date of Patent: Apr. 2, 2024

(54) TRANSMISSION LINE WITH HEAT TRANSFER ABILITY

(71) Applicant: NeuWave Medical, Inc., Madison, WI (US)

(72) Inventors: Daniel W. van der Weide, Madison, WI (US); Fred T. Lee, Jr., Madison, WI (US); Paul F. Laeseke, Madison, WI (US); Christopher L Brace, Madison, WI (US)

(73) Assignee: NeuWave Medical, Inc., Madison, WI (US)

( * ) Notice: Subject to any disclaimer, the term of this patent is extended or adjusted under 35 U.S.C. 154(b) by 1282 days.

(21) Appl. No.: 16/525,067

(22) Filed: Jul. 29, 2019

(65) Prior Publication Data
US 2019/0350652 A1    Nov. 21, 2019

Related U.S. Application Data

(63) Continuation of application No. 11/728,460, filed on Mar. 26, 2007, now Pat. No. 10,363,092.
(Continued)

(51) Int. Cl.
*A61B 18/18* (2006.01)
*A61B 18/00* (2006.01)

(52) U.S. Cl.
CPC .......... *A61B 18/18* (2013.01); *A61B 18/1815* (2013.01); *A61B 2018/00023* (2013.01); *A61B 2018/183* (2013.01)

(58) Field of Classification Search
CPC ...... A61B 18/1815; A61B 2018/00023; A61B 2018/1869; A61B 2018/1861
See application file for complete search history.

(56) References Cited

U.S. PATENT DOCUMENTS 3,800,552 A    4/1974  Sollami
3,838,242 A    9/1974  Goucher
(Continued)

FOREIGN PATENT DOCUMENTS

AU    2015/202149    5/2015
CN    1593353       3/2005
(Continued)

OTHER PUBLICATIONS

Brace, C. et al 'Microwave Ablation with Triaxial Antenna: Results in ex vivo Bovine Liver' IEEE Transactions on Microwave Theory and Techniques, vol. 53, No. 1 Jan. 2005.
(Continued)

*Primary Examiner* — Jaymi E Della
(74) *Attorney, Agent, or Firm* — Casimir Jones, S.C.; Robert A. Goetz

(57) ABSTRACT

The present invention relates to systems and devices for delivering energy to tissue for a wide variety of applications, including medical procedures (e.g., tissue ablation, resection, cautery, vascular thrombosis, treatment of cardiac arrhythmias and dysrhythmias, electrosurgery, tissue harvest, etc.). In particular, the present invention relates to systems and devices for the delivery of energy with heat transfer ability. In some embodiments, the systems and devices also have variable characteristic impedance as a result of the use of heat transfer materials. In certain embodiments, methods are provided for treating a tissue region (e.g., a tumor) through application of energy with the systems and devices of the present invention.

16 Claims, 12 Drawing Sheets

Related U.S. Application Data

(60) Provisional application No. 60/785,467, filed on Mar. 24, 2006.

(56) References Cited

U.S. PATENT DOCUMENTS

| | | |
|---|---|---|
| 3,991,770 A | 11/1976 | LeVeen |
| 4,057,064 A | 11/1977 | Morrison |
| 4,074,718 A | 2/1978 | Morrison |
| 4,312,364 A | 1/1982 | Convert |
| 4,375,220 A | 3/1983 | Matvias |
| 4,446,874 A | 5/1984 | Vaguine |
| 4,494,539 A | 1/1985 | Zenitani |
| 4,534,347 A | 8/1985 | Taylor |
| 4,557,272 A | 12/1985 | Carr |
| 4,586,491 A | 5/1986 | Carpenter |
| 4,589,424 A | 5/1986 | Vaguine |
| 4,601,296 A * | 7/1986 | Yerushalmi ........ A61B 18/1815 604/113 |
| 4,621,642 A | 11/1986 | Chen |
| 4,627,435 A | 12/1986 | Hoskin |
| 4,641,649 A | 2/1987 | Walinsky |
| 4,643,186 A | 2/1987 | Rosen |
| 4,662,383 A | 5/1987 | Sogawa |
| 4,700,716 A | 10/1987 | Kasevich |
| 4,712,559 A | 12/1987 | Turner |
| 4,776,086 A | 10/1988 | Kasevich |
| 4,790,311 A | 12/1988 | Ruiz |
| 4,860,752 A | 8/1989 | Turner |
| 4,880,015 A | 11/1989 | Nierman |
| 4,901,719 A | 2/1990 | Trenconsky |
| 4,945,912 A | 8/1990 | Langberg |
| 4,974,587 A | 12/1990 | Turner |
| 5,007,437 A | 4/1991 | Sterzer |
| 5,026,959 A | 6/1991 | Ito |
| 5,057,104 A | 10/1991 | Chess |
| 5,057,106 A | 10/1991 | Kasevich |
| 5,074,861 A | 12/1991 | Schneider |
| RE33,791 E | 1/1992 | Carr |
| 5,098,429 A | 3/1992 | Sterzer |
| 5,129,396 A | 7/1992 | Rosen |
| 5,150,717 A | 9/1992 | Rosen et al. |
| 5,167,619 A | 12/1992 | Wuchinich |
| 5,211,625 A | 5/1993 | Sakurai |
| 5,213,561 A | 5/1993 | Weinstein |
| 5,246,438 A | 9/1993 | Langberg |
| 5,248,312 A | 9/1993 | Langberg |
| 5,275,597 A | 1/1994 | Higgins |
| 5,277,201 A | 1/1994 | Stern |
| 5,281,213 A | 1/1994 | Midler |
| 5,281,217 A | 1/1994 | Edwards |
| 5,295,955 A | 3/1994 | Rosen |
| 5,300,099 A | 4/1994 | Rudie |
| 5,301,687 A | 4/1994 | Wong |
| 5,314,466 A | 5/1994 | Stern |
| 5,344,418 A | 9/1994 | Ghaffari |
| 5,344,435 A | 9/1994 | Turner |
| 5,348,554 A | 9/1994 | Imran |
| 5,358,515 A | 10/1994 | Hurter |
| 5,364,392 A | 11/1994 | Warner |
| 5,366,490 A | 11/1994 | Edwards |
| 5,369,251 A | 11/1994 | King |
| 5,370,678 A | 12/1994 | Edwards |
| 5,405,346 A | 4/1995 | Grundy |
| 5,431,649 A | 7/1995 | Muller |
| 5,433,740 A | 7/1995 | Yamaguchi |
| 5,456,684 A | 10/1995 | Schmidt |
| 5,462,556 A | 10/1995 | Powers |
| 5,472,423 A | 12/1995 | Gronauer |
| 5,480,417 A | 1/1996 | Hascoet |
| 5,489,256 A | 2/1996 | Adair |
| 5,507,743 A | 4/1996 | Edwards |
| 5,531,677 A | 7/1996 | Lundquist |
| 5,540,649 A | 7/1996 | Bonnell et al. |
| 5,559,295 A | 9/1996 | Sheryll |
| 5,575,794 A | 11/1996 | Walus |
| 5,578,029 A | 11/1996 | Trelles |
| 5,591,227 A | 1/1997 | Dinh |
| 5,597,146 A | 1/1997 | Putman |
| 5,599,295 A | 2/1997 | Rosen |
| 5,599,352 A | 2/1997 | Dinh |
| 5,603,697 A | 2/1997 | Diederich |
| 5,620,479 A | 4/1997 | Diederich |
| 5,643,175 A | 7/1997 | Adair |
| 5,647,871 A | 7/1997 | Levine |
| 5,688,267 A | 11/1997 | Panescu et al. |
| 5,693,082 A | 12/1997 | Warner |
| 5,697,949 A | 12/1997 | Giurtino |
| 5,716,389 A | 2/1998 | Walinsky |
| 5,737,384 A | 4/1998 | Fenn |
| 5,741,249 A | 4/1998 | Moss |
| 5,755,752 A | 5/1998 | Segal |
| 5,755,754 A | 5/1998 | Rudie |
| 5,759,200 A | 6/1998 | Azar |
| 5,776,129 A | 7/1998 | Mersch |
| 5,776,176 A | 7/1998 | Rudie |
| 5,782,827 A | 7/1998 | Gough |
| 5,788,692 A | 8/1998 | Campbell |
| 5,788,694 A | 8/1998 | Vancaillie |
| 5,800,494 A | 9/1998 | Campbell |
| 5,810,803 A | 9/1998 | Moss |
| 5,810,804 A | 9/1998 | Gough |
| 5,849,029 A | 12/1998 | Eckhouse |
| 5,902,251 A | 5/1999 | Vanhooydonk |
| 5,904,709 A | 5/1999 | Arndt |
| 5,921,935 A | 7/1999 | Hickey |
| 5,957,969 A | 9/1999 | Warner |
| 5,963,082 A | 10/1999 | Dick |
| 5,995,875 A | 11/1999 | Biewett |
| 6,002,968 A | 12/1999 | Edwards |
| 6,012,457 A | 1/2000 | Lesh |
| 6,016,811 A | 1/2000 | Knopp |
| 6,026,331 A | 2/2000 | Feldberg |
| 6,044,846 A | 4/2000 | Edwards |
| 6,056,744 A | 5/2000 | Edwards |
| 6,067,475 A | 5/2000 | Graves |
| 6,073,052 A | 6/2000 | Zelickson |
| 6,083,255 A | 7/2000 | Laufer |
| 6,086,529 A | 7/2000 | Arndt |
| 6,091,995 A | 7/2000 | Ingle et al. |
| 6,097,985 A | 8/2000 | Zasevich |
| 6,102,885 A | 8/2000 | Bass |
| 6,104,959 A | 8/2000 | Spertell |
| 6,106,524 A | 8/2000 | Eggers |
| 6,120,496 A | 9/2000 | Whayne et al. |
| 6,165,163 A | 12/2000 | Chien et al. |
| 6,174,307 B1 | 1/2001 | Daniel et al. |
| 6,182,666 B1 | 2/2001 | Dobak, III |
| 6,188,930 B1 | 2/2001 | Carson |
| 6,190,382 B1 | 2/2001 | Ormsby |
| 6,208,903 B1 | 3/2001 | Richards |
| 6,210,323 B1 | 4/2001 | Gilhuly et al. |
| 6,223,085 B1 | 4/2001 | Dann |
| 6,312,427 B1 | 4/2001 | Berube |
| 6,230,060 B1 | 5/2001 | Mawhinney |
| 6,235,022 B1 | 5/2001 | Hallock et al. |
| 6,241,725 B1 | 6/2001 | Cosman |
| 6,245,062 B1 | 6/2001 | Berube |
| 6,246,784 B1 | 6/2001 | Summers |
| 6,246,905 B1 | 6/2001 | Mogul |
| 6,251,128 B1 | 6/2001 | Knopp |
| 6,254,598 B1 | 7/2001 | Edwards |
| 6,273,884 B1 | 8/2001 | Altshuler |
| 6,273,885 B1 | 8/2001 | Koop |
| 6,273,886 B1 | 8/2001 | Edwards et al. |
| 6,277,113 B1 | 8/2001 | Berube |
| 6,287,302 B1 | 9/2001 | Berube |
| 6,306,130 B1 | 10/2001 | Anderson |
| 6,306,132 B1 | 10/2001 | Moorman |
| 6,325,796 B1 | 12/2001 | Berube |
| 6,347,251 B1 | 2/2002 | Deng |
| 6,355,033 B1 | 3/2002 | Moorman |
| 6,364,876 B1 | 4/2002 | Erb |
| 6,383,182 B1 | 5/2002 | Berube |

(56) References Cited

U.S. PATENT DOCUMENTS

| | | |
|---|---|---|
| 6,395,803 B1 | 5/2002 | Angeletakis |
| 6,398,781 B1 | 6/2002 | Goble |
| 6,402,742 B1 | 6/2002 | Blewett |
| 6,427,089 B1 | 7/2002 | Knowlton |
| 6,435,872 B1 | 8/2002 | Nagel |
| 6,461,351 B1 | 10/2002 | Woodruff et al. |
| 6,461,352 B2 | 10/2002 | Morgan |
| 6,471,696 B1 | 10/2002 | Berube |
| 6,500,174 B1 | 12/2002 | Maguire |
| 6,506,189 B1 | 1/2003 | Rittman |
| 6,514,249 B1 | 2/2003 | Maguire |
| 6,524,308 B1 | 2/2003 | Muller |
| 6,527,768 B2 | 3/2003 | Berube |
| 6,530,922 B2 | 3/2003 | Cosman |
| 6,546,077 B2 | 4/2003 | Chornenky |
| 6,575,969 B1 | 6/2003 | Rittman, III |
| 6,577,903 B1 | 6/2003 | Cronin |
| 6,582,426 B2 | 6/2003 | Moorman et al. |
| 6,582,486 B1 | 6/2003 | Delpiano |
| 6,585,733 B2 | 7/2003 | Wellman |
| 6,593,395 B2 | 7/2003 | Angeletakis |
| 6,602,074 B1 | 8/2003 | Suh |
| 6,622,731 B2 | 9/2003 | Daniel |
| 6,635,055 B1 | 10/2003 | Cronin |
| 6,638,277 B2 | 10/2003 | Schaefer et al. |
| 6,652,520 B2 | 11/2003 | Moorman |
| 6,663,625 B1 | 12/2003 | Ormsby |
| 6,666,579 B2 | 12/2003 | Jensen |
| 6,683,625 B2 | 1/2004 | Muthusamy et al. |
| 6,694,163 B1 | 2/2004 | Vining |
| 6,699,240 B2 | 3/2004 | Francischelli |
| 6,709,271 B2 | 3/2004 | Yin |
| 6,740,107 B2 | 5/2004 | Loeb |
| 6,749,606 B2 | 6/2004 | Keast |
| 6,752,767 B2 | 6/2004 | Turovskiy |
| D493,531 S | 7/2004 | Padain |
| 6,770,070 B1 | 8/2004 | Balbierz |
| 6,780,178 B2 | 8/2004 | Palanker |
| 6,673,068 B1 | 10/2004 | Berube |
| 6,802,840 B2 | 10/2004 | Chin |
| 6,817,976 B2 | 11/2004 | Rovegno |
| 6,817,999 B2 | 11/2004 | Berube |
| 6,823,218 B2 | 11/2004 | Berube |
| 6,837,712 B2 | 1/2005 | Qian |
| 6,847,848 B2 | 1/2005 | Sterzer |
| 6,849,075 B2 | 2/2005 | Bertolero et al. |
| 6,852,091 B2 | 2/2005 | Edwards |
| 6,866,624 B2 | 3/2005 | Chornenky |
| 6,866,663 B2 | 3/2005 | Edwards |
| 6,869,431 B2 | 3/2005 | Maguire |
| 6,878,147 B2 | 4/2005 | Prakash |
| 6,890,968 B2 | 5/2005 | Angeletakis |
| 6,893,436 B2 | 5/2005 | Woodard |
| 6,898,454 B2 | 5/2005 | Atalar |
| D507,649 S | 7/2005 | Padain |
| 6,918,905 B2 | 7/2005 | Neuberger |
| 6,924,325 B2 | 8/2005 | Qian |
| 6,957,108 B2 | 10/2005 | Turner |
| 6,962,586 B2 | 11/2005 | Berube |
| 6,972,016 B2 | 12/2005 | Hill |
| 6,976,986 B2 | 12/2005 | Berube |
| 6,994,546 B2 | 2/2006 | Fischer |
| 7,022,105 B1 | 4/2006 | Edwards |
| 7,033,352 B1 | 4/2006 | Gauthier |
| 7,097,641 B1 | 8/2006 | Arless |
| 7,101,369 B2 | 9/2006 | van der Weide |
| 7,115,126 B2 | 10/2006 | Berube et al. |
| 7,128,739 B2 | 10/2006 | Prakash |
| 7,142,633 B2 | 11/2006 | Eberhard |
| 7,147,632 B2 | 12/2006 | Prakash |
| 7,153,298 B1 | 12/2006 | Cohen |
| 7,156,842 B2 | 1/2007 | Sartor et al. |
| 7,160,289 B2 | 1/2007 | Cohen |
| 7,160,292 B2 | 1/2007 | Moorman |
| 7,182,762 B2 | 2/2007 | Bortkiewicz |
| 7,184,824 B2 | 2/2007 | Hashimshony |
| 7,197,363 B2 | 3/2007 | Prakash |
| 7,233,820 B2 | 6/2007 | Gilboa |
| 7,244,254 B2 | 7/2007 | Brace |
| 7,263,997 B2 | 9/2007 | Madsen et al. |
| 7,266,407 B2 | 9/2007 | Li |
| 7,282,049 B2 | 10/2007 | Orszulak |
| 7,311,703 B2 | 12/2007 | Turovskiy |
| 7,318,824 B2 | 1/2008 | Prakash |
| 7,324,104 B1 | 1/2008 | Bitter |
| 7,331,960 B2 | 2/2008 | Schaer |
| 7,381,208 B2 | 6/2008 | van der Walt |
| 7,400,929 B2 | 7/2008 | Zelickson et al. |
| 7,402,140 B2 | 7/2008 | Spero |
| 7,410,484 B2 | 8/2008 | Littrup |
| 7,467,015 B2 | 12/2008 | van der Weide |
| 7,473,219 B1 | 1/2009 | Glenn |
| 7,527,623 B2 | 5/2009 | Prakash |
| 7,594,313 B2 | 9/2009 | Prakash |
| 7,601,149 B2 | 10/2009 | DiCarlo et al. |
| 7,625,369 B2 | 12/2009 | Abboud |
| 7,722,620 B2 | 5/2010 | Truckai |
| 7,731,677 B2 | 6/2010 | Sakurai |
| 7,815,637 B2 | 10/2010 | Ormsby |
| 7,826,904 B2 | 11/2010 | Appling |
| 7,862,559 B2 | 1/2011 | Prakash |
| 7,875,024 B2 | 1/2011 | Turovskiy |
| 8,035,570 B2 | 10/2011 | Prakash |
| 8,059,059 B2 | 11/2011 | Bonn |
| 8,093,500 B2 | 1/2012 | Deborski |
| 8,109,895 B2 | 2/2012 | Williams et al. |
| 8,147,511 B2 | 4/2012 | Perry |
| 8,152,799 B2 | 4/2012 | Ormsby |
| 8,155,418 B2 | 4/2012 | Delso |
| 8,235,981 B2 | 8/2012 | Prakash |
| 8,357,148 B2 | 1/2013 | Boulais |
| 8,403,924 B2 | 3/2013 | Behnke |
| 8,430,871 B2 | 4/2013 | Brannan |
| 8,515,554 B2 | 8/2013 | Carr |
| 8,523,854 B2 | 9/2013 | Willyard |
| 8,540,710 B2 | 9/2013 | Johnson |
| 8,574,227 B2 | 11/2013 | Hancock |
| 8,643,561 B2 | 2/2014 | Prakash |
| 8,653,828 B2 | 2/2014 | Hancock |
| 8,655,454 B2 | 2/2014 | Prakash |
| 8,672,932 B2 | 3/2014 | van der Weide |
| 8,747,398 B2 | 6/2014 | Behnke |
| 8,764,744 B2 | 7/2014 | Brannan |
| 8,932,281 B2 | 1/2015 | Brannan |
| 8,934,989 B2 | 1/2015 | Ormsby |
| 8,945,111 B2 | 2/2015 | Brannan et al. |
| 8,968,290 B2 | 3/2015 | Brannan |
| 9,008,793 B1 | 4/2015 | Cosman |
| 9,011,421 B2 | 4/2015 | Brannan |
| 9,017,319 B2 | 4/2015 | Brannan |
| 9,041,616 B2 | 5/2015 | Prakash |
| 9,072,532 B2 | 7/2015 | van der Weide |
| 9,113,926 B2 | 8/2015 | Brannan |
| 9,119,649 B2 | 9/2015 | van der Weide |
| 9,119,650 B2 | 9/2015 | Brannan |
| 9,161,811 B2 | 10/2015 | Cronin |
| 9,173,706 B2 | 11/2015 | Rossetto |
| 9,192,436 B2 | 11/2015 | Willyard |
| 9,192,438 B2 | 11/2015 | Thiel |
| 9,198,725 B2 | 12/2015 | Willyard |
| 9,220,441 B2 | 12/2015 | Yoo |
| 2001/0020166 A1 | 9/2001 | Daly et al. |
| 2001/0039416 A1 | 11/2001 | Moorman et al. |
| 2001/0049524 A1 | 12/2001 | Morgan |
| 2002/0022836 A1 | 2/2002 | Goble |
| 2002/0026187 A1 | 2/2002 | Swanson et al. |
| 2002/0040185 A1 | 4/2002 | Atalar |
| 2002/0072742 A1 | 6/2002 | Schaefer |
| 2002/0087151 A1 | 7/2002 | Mody et al. |
| 2002/0087157 A1 | 7/2002 | Sliwa et al. |
| 2002/0173780 A1 | 11/2002 | Altshuler |
| 2002/0183740 A1 | 12/2002 | Edwards |
| 2003/0032951 A1 | 2/2003 | Rittman et al. |
| 2003/0060813 A1 | 3/2003 | Loeb |

(56) References Cited

U.S. PATENT DOCUMENTS

| | | |
|---|---|---|
| 2003/0065317 A1 | 4/2003 | Rudie |
| 2003/0088242 A1 | 5/2003 | Prakash |
| 2003/0120268 A1 | 6/2003 | Bertolero |
| 2004/0030367 A1 | 2/2004 | Yamaki et al. |
| 2004/0068208 A1 | 4/2004 | Cimino et al. |
| 2004/0082859 A1 | 4/2004 | Schaer |
| 2004/0158237 A1 | 8/2004 | Abboud |
| 2004/0186517 A1 | 9/2004 | Hill et al. |
| 2004/0199154 A1 | 10/2004 | Nahon |
| 2004/0215131 A1 | 10/2004 | Sakurai |
| 2004/0215294 A1 | 10/2004 | Littrup |
| 2004/0243004 A1 | 12/2004 | Carr |
| 2004/0243200 A1 | 12/2004 | Turner |
| 2004/0267248 A1 | 12/2004 | Duong |
| 2005/0011885 A1 | 1/2005 | Seghatol |
| 2005/0015081 A1* | 1/2005 | Turovskiy ............ A61B 18/18 607/156 |
| 2005/0075629 A1 | 4/2005 | Chapelon |
| 2005/0107870 A1 | 5/2005 | Wang |
| 2005/0109900 A1 | 5/2005 | Schilt et al. |
| 2005/0113824 A1 | 5/2005 | Sartor |
| 2005/0143726 A1 | 6/2005 | Bortkiewicz |
| 2005/0149010 A1 | 7/2005 | Turovskiy |
| 2005/0165389 A1 | 7/2005 | Swain |
| 2005/0177209 A1 | 8/2005 | Leung et al. |
| 2005/0245919 A1 | 11/2005 | van der Weide |
| 2005/0245920 A1 | 11/2005 | Vitullo et al. |
| 2006/0064083 A1 | 3/2006 | Khalaj et al. |
| 2006/0079886 A1 | 4/2006 | Orszulak et al. |
| 2006/0094956 A1 | 5/2006 | Vismanathan |
| 2006/0106281 A1 | 5/2006 | Boulais |
| 2006/0122625 A1 | 6/2006 | Truckai |
| 2006/0129140 A1 | 6/2006 | Todd et al. |
| 2006/0155270 A1 | 7/2006 | Hancock |
| 2006/0171506 A1* | 8/2006 | Lovoi .................... H01J 35/32 378/130 |
| 2006/0189973 A1 | 8/2006 | van der Weide |
| 2006/0200026 A1 | 9/2006 | Wallace et al. |
| 2006/0200120 A1 | 9/2006 | DiCarlo |
| 2006/0224220 A1 | 10/2006 | Zelickson |
| 2006/0264921 A1 | 11/2006 | Deutsch et al. |
| 2006/0289528 A1 | 12/2006 | Chiu |
| 2007/0016180 A1 | 1/2007 | Lee, Jr. et al. |
| 2007/0021741 A1 | 1/2007 | Abboud et al. |
| 2007/0066972 A1 | 3/2007 | Ormsby |
| 2007/0203551 A1 | 8/2007 | Cronin |
| 2007/0208389 A1 | 9/2007 | Amundson et al. |
| 2007/0230757 A1 | 10/2007 | Trachtenberg et al. |
| 2007/0270924 A1 | 11/2007 | McCann et al. |
| 2007/0276362 A1 | 11/2007 | Rioux |
| 2007/0282319 A1 | 12/2007 | van der Weide |
| 2007/0288079 A1 | 12/2007 | van der Weide |
| 2008/0033424 A1 | 2/2008 | Van Der Weide |
| 2008/0045938 A1 | 2/2008 | Van Der Weide et al. |
| 2008/0114345 A1 | 5/2008 | Arless et al. |
| 2008/0147056 A1 | 6/2008 | Van der Weide |
| 2008/0161890 A1 | 7/2008 | Lafontaine |
| 2008/0188868 A1 | 8/2008 | Weitzner et al. |
| 2008/0188869 A1 | 8/2008 | Weitzner et al. |
| 2008/0188871 A1 | 8/2008 | Smith et al. |
| 2008/0188890 A1 | 8/2008 | Weitzner et al. |
| 2008/0195226 A1 | 8/2008 | Williams et al. |
| 2008/0221391 A1 | 9/2008 | Weitzner et al. |
| 2008/0243176 A1 | 10/2008 | Weitzner et al. |
| 2009/0005766 A1 | 1/2009 | Brannan |
| 2009/0054962 A1 | 2/2009 | Lefler |
| 2009/0076492 A1 | 3/2009 | Behnke |
| 2009/0118725 A1 | 5/2009 | Auth et al. |
| 2009/0187180 A1 | 7/2009 | Brannan |
| 2009/0187186 A1 | 7/2009 | Jakus |
| 2009/0196480 A1 | 8/2009 | Nields et al. |
| 2009/0222002 A1 | 9/2009 | Bonn et al. |
| 2009/0281536 A1 | 11/2009 | Beckman et al. |
| 2009/0306644 A1 | 12/2009 | Mayse et al. |
| 2010/0023866 A1 | 1/2010 | Peck et al. |
| 2010/0045558 A1 | 2/2010 | Rossetto |
| 2010/0045559 A1 | 2/2010 | Rossetto |
| 2010/0076424 A1 | 3/2010 | Carr |
| 2010/0081928 A1 | 4/2010 | Hyde et al. |
| 2010/0137796 A1 | 6/2010 | Perry et al. |
| 2010/0228244 A1 | 9/2010 | Hancock |
| 2010/0268223 A1 | 10/2010 | Coe |
| 2010/0286791 A1 | 11/2010 | Goldsmith |
| 2010/0292766 A1 | 11/2010 | Duong |
| 2010/0305561 A1 | 12/2010 | Prakash et al. |
| 2010/0312095 A1 | 12/2010 | Jenkins |
| 2010/0312096 A1 | 12/2010 | Guttman |
| 2010/0317962 A1 | 12/2010 | Jenkins |
| 2011/0077635 A1 | 3/2011 | Bonn |
| 2011/0118723 A1 | 5/2011 | Turner et al. |
| 2011/0118725 A1 | 5/2011 | Mayse |
| 2011/0213352 A1 | 9/2011 | Lee et al. |
| 2011/0238060 A1 | 9/2011 | Lee, Jr. |
| 2011/0238061 A1 | 9/2011 | van der Weide |
| 2011/0257647 A1 | 10/2011 | Mayse |
| 2011/0301587 A1 | 12/2011 | Deem |
| 2012/0016358 A1 | 1/2012 | Mayse |
| 2012/0053577 A1 | 3/2012 | Lee et al. |
| 2012/0116286 A1 | 5/2012 | Williams et al. |
| 2012/0182134 A1 | 7/2012 | Doyle |
| 2012/0194409 A1 | 8/2012 | Brannan |
| 2012/0203216 A1 | 8/2012 | Mayse et al. |
| 2012/0203222 A1 | 8/2012 | Mayse |
| 2012/0209257 A1 | 8/2012 | van der Weide |
| 2012/0209261 A1 | 8/2012 | Mayse |
| 2012/0209296 A1 | 8/2012 | Martin |
| 2012/0232544 A1 | 9/2012 | Willyard |
| 2012/0232549 A1 | 9/2012 | Willyard |
| 2012/0310228 A1 | 12/2012 | Bonn et al. |
| 2012/0316551 A1 | 12/2012 | can der Weide |
| 2012/0316552 A1 | 12/2012 | Mayse |
| 2012/0316559 A1 | 12/2012 | Mayse |
| 2013/0004037 A1 | 1/2013 | Scheuering |
| 2013/0023866 A1 | 1/2013 | Stringham |
| 2013/0072924 A1 | 3/2013 | Burgener |
| 2013/0116679 A1 | 5/2013 | van der Weide et al. |
| 2013/0123598 A1 | 5/2013 | Jenkins |
| 2013/0131496 A1 | 5/2013 | Jenkins |
| 2013/0165915 A1 | 6/2013 | Thiel |
| 2013/0259335 A1 | 10/2013 | Mallya et al. |
| 2013/0306543 A1 | 11/2013 | Beisser |
| 2013/0338530 A1 | 12/2013 | Kassab |
| 2014/0005706 A1 | 1/2014 | Gelfand et al. |
| 2014/0046174 A1 | 2/2014 | Ladtkow et al. |
| 2014/0046176 A1 | 2/2014 | Ladtkow |
| 2014/0152656 A1 | 6/2014 | Yoo |
| 2014/0163664 A1 | 6/2014 | Goldsmith et al. |
| 2014/0276033 A1 | 9/2014 | Brannan |
| 2014/0276200 A1 | 9/2014 | Brannan |
| 2015/0148792 A1 | 5/2015 | Kim |
| 2015/0150628 A1 | 6/2015 | Buysse |
| 2015/0164587 A1 | 6/2015 | Bonn et al. |
| 2015/0190193 A1 | 7/2015 | Mayse |
| 2015/0250540 A1 | 9/2015 | Behdad et al. |
| 2015/0351839 A1 | 12/2015 | Brannan |
| 2015/0374438 A1 | 12/2015 | van der Weide |

FOREIGN PATENT DOCUMENTS

| | | |
|---|---|---|
| CN | 1703168 | 11/2005 |
| CN | 2753408 | 1/2006 |
| CN | 201267529 | 7/2009 |
| CN | 101511295 | 8/2009 |
| CN | 101563042 | 10/2009 |
| EP | 1186274 | 3/2002 |
| EP | 1265532 | 12/2002 |
| EP | 2388039 | 11/2003 |
| EP | 1395190 | 3/2004 |
| EP | 1450710 | 9/2004 |
| EP | 1499251 | 1/2005 |
| EP | 2406521 | 4/2005 |
| EP | 1542607 | 6/2005 |
| EP | 1723922 | 11/2006 |
| EP | 2098184 | 9/2009 |

(56) References Cited

FOREIGN PATENT DOCUMENTS

| | | |
|---|---|---|
| EP | 2295000 | 3/2011 |
| EP | 2316370 | 5/2011 |
| EP | 1659969 | 10/2012 |
| JP | 10-192286 | 7/1998 |
| JP | 2002-541884 | 12/2002 |
| JP | 2003-530139 | 10/2003 |
| JP | 2003-534037 | 11/2003 |
| JP | 2004-188179 | 7/2004 |
| JP | 2005-522274 | 7/2005 |
| JP | 2007-029457 | 2/2007 |
| JP | 2007-532024 | 11/2007 |
| JP | 2008-142467 | 6/2008 |
| JP | 2009-006150 | 1/2009 |
| JP | 2009-521264 | 6/2009 |
| JP | 2009-521967 | 6/2009 |
| JP | 2009-207898 | 9/2009 |
| JP | 2009-285463 | 12/2009 |
| JP | 2010-505573 | 2/2010 |
| JP | 2010-050975 | 3/2010 |
| JP | 2011-511538 | 4/2011 |
| JP | 2011-092720 | 5/2011 |
| JP | 2011-152414 | 8/2011 |
| WO | WO 1992/004934 | 4/1992 |
| WO | WO 1993/009845 | 5/1993 |
| WO | WO 1995/004385 | 9/1995 |
| WO | WO 1997/048449 | 12/1997 |
| WO | WO 1999/056643 | 11/1999 |
| WO | WO 2000/057811 | 10/2000 |
| WO | WO 2001/070114 | 9/2001 |
| WO | WO 2003/039385 | 5/2003 |
| WO | WO 2003/086190 | 10/2003 |
| WO | WO 2003/086498 | 10/2003 |
| WO | WO 2003/088806 | 10/2003 |
| WO | WO 2003/088858 | 10/2003 |
| WO | WO 2004/004586 | 1/2004 |
| WO | WO 2004/026122 | 1/2004 |
| WO | WO 2004/033039 | 4/2004 |
| WO | WO 2004/084748 | 10/2004 |
| WO | WO 2004/112628 | 12/2004 |
| WO | WO 2005/011049 | 2/2005 |
| WO | WO 2005/034783 | 4/2005 |
| WO | WO 2005/110265 | 11/2005 |
| WO | WO 2006/002843 | 1/2006 |
| WO | WO 2006/002943 | 1/2006 |
| WO | WO 2006/004585 | 1/2006 |
| WO | WO 2006/005579 | 1/2006 |
| WO | WO 2006/008481 | 1/2006 |
| WO | WO 2006/084676 | 8/2006 |
| WO | WO 2006/122149 | 11/2006 |
| WO | WO 2006/127847 | 11/2006 |
| WO | WO 2007/076924 | 7/2007 |
| WO | WO 2007/112103 | 10/2007 |
| WO | WO 2008/008545 | 1/2008 |
| WO | WO 2008/044013 | 4/2008 |
| WO | WO 2008/142686 | 11/2008 |
| WO | WO 2010/067360 | 6/2010 |
| WO | WO 2011/008903 | 1/2011 |
| WO | WO 2011/017168 | 2/2011 |
| WO | WO 2011/140087 | 11/2011 |
| WO | WO 2013/173481 | 11/2013 |

OTHER PUBLICATIONS

European Search Report dated Mar. 9, 2015, EP Patent Application No. 14189493.1.
Extended European Search Report re: 11778168 dated Sep. 24, 2013.
Golio, 'The RF and microwave handbook' Edition 2 Published by CRC Press 2001 ISBN 0849338592X, 97808493859626.
Guy, AW (1971) IEEE Trans. Microwave Theory Tech. 19 pp. 205-214.
Head, Hayden W., et al., "Thermal Ablation for Hepatocellular Carcinoma," Gastroenterology, 2004:127:S167-S178.
International Preliminary Report on Patentability re: PCT/US2010/043558 dated Jan. 31, 2012.
International Preliminary Report on Patentability re: PCT/US2011/035000 dated Nov. 6, 2012.
International Preliminary Report on Patentability re: PCT/US2012/071310 dated Aug. 19, 2014.
International Search Report & Written Opinion, International Patent Application No. PCT/US2017/027424, dated Oct. 9, 2017.
International Search Report on Patentability re: PCT/US2007/016082 dated Jul. 21, 2008.
International Search Report PCT US/2006/028821 dated Mar. 21, 2007.
International Search Report PCT/US2005/014534 dated Nov. 29, 2005.
International Search Report PCT/US2006/017981 dated Sep. 7, 2006.
International Search Report PCT/US2006/033341 dated Aug. 17, 2007.
U.S. Appl. No. 11/440,331, filed May 24, 2006.
U.S. Appl. No. 11/452,637, filed Jun. 14, 2006.
U.S. Appl. No. 11/502,783, filed Aug. 11, 2006.
U.S. Appl. No. 11/514,628, filed Sep. 1, 2006.
U.S. Appl. No. 11/728,428, filed Mar. 26, 2007.
U.S. Appl. No. 11/728,457, filed Mar. 26, 2007.
U.S. Appl. No. 11/728,460, filed Mar. 26, 2007.
U.S. Appl. No. 60/679,722, filed May 10, 2005.
U.S. Appl. No. 60/785,466, filed Mar. 24, 2006.
U.S. Appl. No. 60/785,467, filed Mar. 24, 2006.
U.S. Appl. No. 60/785,690, filed Mar. 24, 2006.
U.S. Appl. No. 60/831,055, filed Jul. 14, 2006.
International Search Report, PCT/US06/032811, dated Jan. 25, 2007.
International Search Report, PCT/US06/031644, dated Aug. 17, 2007.
"Carbon dioxide." Carbon dioxide—New World Encyclopedia. Web. <http://www.newworldencyclopedia.org/entry/Carbon_dioxide>.

\* cited by examiner

FIG. 1A
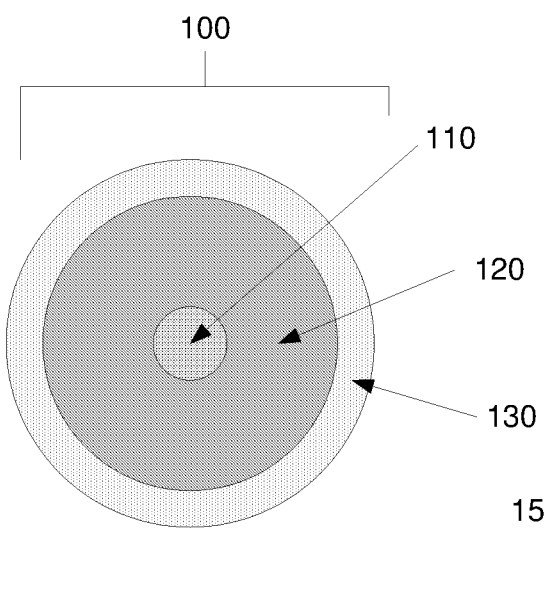
FIG. 1B
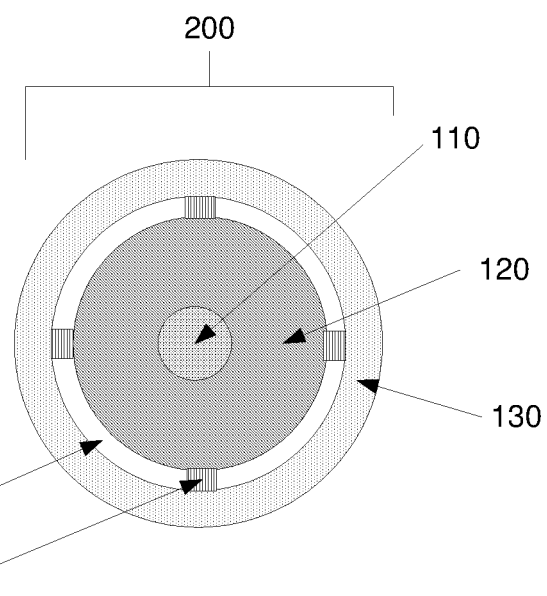
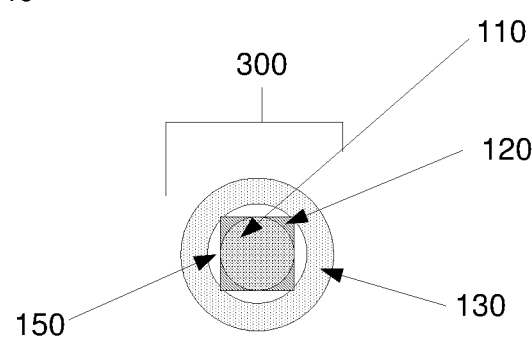
FIG. 1C

TRANSMISSION LINE WITH HEAT TRANSFER ABILITY

The present application is a continuation of U.S. patent application Ser. No. 11/728,460, filed Mar. 26, 2007, allowed as U.S. Pat. No. 10,363,092, which claims priority to U.S. Provisional Application Ser. No. 60/785,467, filed Mar. 24, 2006, the entire contents of which are herein incorporated by reference in their entries.

FIELD OF THE INVENTION

The present invention relates to systems and devices for delivering energy to tissue for a wide variety of applications, including medical procedures (e.g., tissue ablation, resection, cautery, vascular thrombosis, treatment of cardiac arrhythmias and dysrhythmias, electrosurgery, tissue harvest, etc.). In particular, the present invention relates to systems and devices for the delivery of energy with heat transfer ability. In some embodiments, the systems and devices also have variable characteristic impedance as a result of the use of heat transfer materials. In certain embodiments, methods are provided for treating a tissue region (e.g., a tumor) through application of energy with the systems and devices of the present invention.

BACKGROUND

Ablation is an important therapeutic strategy for treating certain tissues such as benign and malignant tumors, cardiac arrhythmias, cardiac dysrhythmias and tachycardia. Most approved ablation systems utilize radio frequency (RF) energy as the ablating energy source. Accordingly, a variety of RF based catheters and power supplies are currently available to physicians. However, RF energy has several limitations, including the rapid dissipation of energy in surface tissues resulting in shallow "burns" and failure to access deeper tumor or arrhythmic tissues. Another limitation of RF ablation systems is the tendency of eschar and clot formation to form on the energy emitting electrodes which limits the further deposition of electrical energy.

Microwave energy is an effective energy source for heating biological tissues and is used in such applications as, for example, cancer treatment and preheating of blood prior to infusions. Accordingly, in view of the drawbacks of the traditional ablation techniques, there has recently been a great deal of interest in using microwave energy as an ablation energy source. The advantage of microwave energy over RF is the deeper penetration into tissue, insensitivity to charring, lack of necessity for grounding, more reliable energy deposition, faster tissue heating, and the capability to produce much larger thermal lesions than RF, which greatly simplifies the actual ablation procedures. Accordingly, there are a number of devices under development that utilize electromagnetic energy in the microwave frequency range as the ablation energy source (see, e.g., U.S. Pat. Nos. 4,641,649, 5,246,438, 5,405,346, 5,314,466, 5,800,494, 5,957,969, 6,471,696, 6,878,147, and 6,962,586; each of which is herein incorporated by reference in their entireties).

Unfortunately, current devices configured to deliver microwave energy have drawbacks. For example, current devices produce relatively small lesions because of practical limits in power and treatment time. Current devices have power limitations in that the power carrying capacity of the feedlines is small. Larger diameter feedlines are undesirable, however, because they are less easily inserted percutaneously and may increase procedural complication rates. In addition, heating of the feedline at high powers can lead to burns around the area of insertion for the device.

Improved systems and devices for delivering energy to a tissue region are needed. In addition, improved systems and devices capable of delivering microwave energy without corresponding microwave energy loss are needed. In addition, systems and devices capable of percutaneous delivery of microwave energy to a subject's tissue without undesired tissue burning are needed. Furthermore, systems for delivery of desired amounts of microwave energy without requiring physically large invasive components are needed.

SUMMARY OF THE INVENTION

The present invention relates to systems and devices for delivering energy to tissue for a wide variety of applications, including medical procedures (e.g., tissue ablation, resection, cautery, vascular thrombosis, intraluminal ablation of a hollow viscus, cardiac ablation for treatment of arrhythmias, electrosurgery, tissue harvest, cosmetic surgery, intraocular use, etc.). In particular, the present invention relates to systems and devices for the delivery of energy with heat transfer ability. In some embodiments, the systems and devices also have variable characteristic impedance as a result of the use of heat transfer materials. In certain embodiments, methods are provided for treating a tissue region (e.g., a tumor) through application of energy with the systems and devices of the present invention.

The present invention provides a variety of heat transfer mechanisms. In some embodiments, heat transfer is provided in small diameter devices. For example, in some embodiments, the outer diameter of the device is equivalent to, or smaller than, a 16-gauge needle (e.g., equal or smaller than a 17-gauge needles, a 20-gauge needle, etc.). Embodiments of the present invention provide configurations of the devices that balance energy delivery, heat management, and size. Existing devices, to provide appropriate energy delivery and heat management, are large in diameter, making them undesirable or unsuitable for many applications. In some embodiments, the present invention provides small diameter devices with optimized energy and heating characteristics by providing a cooling material within a coaxial or triaxial cable. For example, in some embodiments, the cooling material is provided within an inner conductor, within a dielectric material separating an inner and outer conductor of a coaxial cable (or central conductor of a triaxial cable), between an inner conductor and dielectric material, between dielectric material and outer conductor of a coaxial cable (or central conductor of a triaxial cable), between the outer two conductors of a triaxial cable, or outside of the outmost conductor of a coaxial or triaxial cable. Examples of some such embodiments are described in more detail below. In some embodiments, space is created for the cooling material, while maintaining the small diameter, by one or more of: a) removing all of or a portion of a dielectric material; b) removing a portion of an inner, central, or outer conductor; c) using thin conductive coatings as conductors; and d) using deformable tubing to carry cooling material within a coaxial or triaxial cable. In some embodiments, the coolant material is directly flowed through a created space. In other embodiments one or more tubes is provided in the space and coolant is flowed in the tube(s) and/or in the tube(s) and the space outside of the tube(s). In some embodiments, cooling material is provided in one direction (e.g., down the device or up the device) through a tube and the opposition direction outside of a tube. The tubes may be rigid or deformable. For example, in some embodiments, an inner conductor is contained within a minimal amount of dielectric material, the dielectric material is coated with a thin conductive film or is covered in a conductive foil so as to provide a coaxial structure, one or more deformable tubes are assembled outside of the film or foil, and a conductive outer member, having a small outer diameter, is placed of the assembly to provide a triaxial device having a small diameter combined with suitable energy delivery and heat management capabilities. By providing sufficient cooling, in a small diameter device, high amounts of power can be sent through the device without overheating, permitting, for example, tissue ablation that would otherwise only be achievable with larger diameter devices. In some embodiments, the tube for conducting coolant is replaced by a fiber whose wicking action enables the flow of coolant in a space-efficient manner.

In some embodiments, the cooling material is provided along only a portion of an energy delivery device. For example, in some embodiments, an energy delivery device comprises a distal tip, an antenna connected to the tip and configured to deliver energy, a feed line that connects to the antenna on the proximal end of the antenna, and a handle at the proximal end of the feed line. In some embodiments, only the handle is contacted with the cooling material. In some embodiments, only the feed line, or portion thereof (e.g., 90% of the length thereof or less, 80%, 70%, 60%, 50%, 40%, etc.), is contacted with the cooling material. In some embodiments, both the handle and the feed line, or a portion thereof, is contacted with the cooling material. In some embodiments, the antenna and/or tip are not contacted with the cooling material (e.g., the cooling material is only flowed to the feed line, and does not travel a sufficient length of the device to reach the antenna).

In some embodiments, the systems, devices, and methods of the present invention provide coaxial transmission lines that allow cooling by circulation of a coolant material through the coaxial transmission line (e.g., circulation of a coolant material through coolant tubes positioned within the coaxial cable) (e.g., through flowing of a coolant material through the dielectric of the coaxial component). In some embodiments, the devices are configured to minimize the diameter of the device, while permitting the passage of the coolant. This is accomplished, in some embodiments, by positioning of deformable coolant tubes (e.g., Kapton tubes) within the coaxial cable. In such embodiments, a triaxial cable comprises a dielectric material positioned between an inner conductor and a middle coaxial shield, and deformable coolant tubes positioned between the middle coaxial shield and an outer conductor. The devices are not limited to a particular middle coaxial shield. In some embodiments, the middle coaxial shield is a thin (e.g., 0.25 mm, 0.5 mm, 1.0 mm, 1.2 mm, 1.4 mm, 1.6 mm, 2.5 mm, etc.) flexible metal (e.g., copper). The devices are not limited to particular coolant tubes. In some embodiments, the coolant tubes are deformable such that upon positioning within a coaxial tube, the tubes will deform but retain an ability to circulate a coolant material (e.g., nitrogen, carbon dioxide, water). In some embodiments, the coolant tubes are Kapton tubes or similar polymer films. As such, the devices providing coolant tubes provide not only an ability to control the temperature of the device (e.g., through circulation of coolant material through the coolant tubes), but also provide an ability to retain its small size (e.g., due to the use of deformable coolant tubes that do not increase the overall diameter of the device).

In some embodiments, the devices are configured to minimize the diameter of the device, while permitting the passage of the coolant, by replacing strips of a solid dielectric material with channels through which a coolant is transferred. In some embodiments, the channels are generated by stripping the dielectric material along the length of the coaxial cable from one or more (e.g., two, three, four) zones. With the removed portions of the dielectric material creating channels for transfer of the coolant, the stripped component fits within a smaller outer conductor than it did prior to removal of the dielectric material (see FIG. 1C, element 300). This provides for smaller devices with all of the advantages derived therefrom. In some embodiments where multiple channels are employed, coolant transfer may be in alternative directions through one or more of the channels. An advantage of the devices is that the diameter of the coaxial cable does not need to be increased to accommodate coolant. This permits the use of cooled devices that are minimally invasive and permits access to regions of a body that are otherwise inaccessible or accessible only with undesired risk. The use of coolant also permits greater energy delivery and/or energy deliver for prolonged periods of time.

The systems, devices, and methods of the present invention further allow for adjustment of the characteristic impedance of the coaxial transmission line. In particular, the dielectric properties of the coolant (or of a non-coolant material that is passed through the coolant tubes and/or channel(s)) may be adjusted to alter the bulk complex permittivity of the dielectric medium separating the outer and inner conductors. In some embodiments, changes in the characteristic impedance are made during a procedure to, for example, optimize energy delivery, tissue effects, temperature, or other desired properties of the system, device, or application. In other embodiments, a flow material is selected prior to a procedure based on the desired parameters and maintained throughout the entire procedure. Thus, the present invention provides systems, devices, and methods that allow an antenna radiating in a changing dielectric environment to be adjusted to resonate in the changing environment to, for example, allow adaptive tuning of the antenna to ensure peak efficiency of operation. As desired, the fluid flow also allows heat transfer to and from the coaxial cable. The present invention is not limited by the means by which the characteristic impedance is altered. In some embodiments, the coolant tubes and/or channels or hollowed out areas contain a vacuum or partial vacuum. In some embodiments, impedance is varied by filling the vacuum with a material (e.g., any material that provides the desired result). Adjustments may be made at one or more time points or continuously.

The present invention is not limited by the method by which material is flowed through the dielectric. In some embodiments, channels are used. In some embodiments, the channel is in contact with both the inner and outer conductors (i.e., entirely removes solid dielectric material from the region so that the flowed material contacts both the inner and outer conductors when flowed through the channel). In some embodiments, the channel is cut through only a portion of the dielectric material so that the flowed material is in contact with either the inner or outer conductor and the remaining dielectric material. In some embodiments, the channels are linear along the length of the coaxial cable. In some embodiments, the channels are non-linear. In some embodiments, where more than one channel is used, the channels run parallel to one another. In other embodiments, the channels are not parallel. In some embodiments, the channels cross one another. In some embodiments, the channels remove over 50% (e.g., 60%, 70%, 80%, etc.) of the solid dielectric material. In some embodiments, the channels remove substantially all of the solid dielectric material.

The present invention is not limited by the nature of the material that is flowed through the dielectric material. In some embodiments, the material is selected to maximize the ability to control the characteristic impedance of the device, to maximize heat transfer to or from the coaxial cable, or to optimize a combination of control of the characteristic impedance and heat transfer. In some embodiments, the material that is flowed through the dielectric material is a liquid. In some embodiments, the material is a gas. In some embodiments, the material is a combination of liquid or gas. In some embodiments, the liquid and/or gas is provided at the respective critical point temperature. The present invention is not limited to the use of liquids or gasses. In some embodiments, the material is a slurry, a gel, or the like. In some embodiments, a coolant fluid is used. Any coolant fluid now known or later developed may be used. Exemplary coolant fluids include, but are not limited to, one or more of or combinations of, water, glycol, air, inert gasses, carbon dioxide, nitrogen, helium, sulfur hexafluoride, organic chemical solutions (e.g., ethylene glycol, diethylene glycol, or propylene glycol), oils (e.g., mineral oils, silicone oils, fluorocarbon oils), liquid metals, freons, halomethanes, liquified propane, other haloalkanes, anhydrous ammonia, sulfur dioxide.

In some embodiments, the systems, methods, and devices of the present invention are configured to permit control over the parameters of fluid infusion through the device. In some embodiments, the device is manually adjusted by the user (e.g., a treating physician or technician) as desired. In some embodiments, the adjustments are automated. In some embodiments, the devices are configured with or used with sensors that provide information to the user or the automated systems (e.g., comprising processors and/or software configured for receiving the information and adjusting fluid infusion or other device parameters accordingly). Parameters that may be regulated include, but are not limited to, speed of infusion of the fluid, concentration of ions or other components that affect the properties of the fluid (e.g., dielectric properties, heat transfer properties, flow rate, etc.), temperature of the fluid, type of fluid, mixture ratios (e.g., mixtures of gas/fluid for precise tuning or cooling). Thus, the present invention provides systems, devices, and methods employing a feed-back loop that can change one or more desired parameters to tune the device (e.g., antenna) more accurately, or speed up the infusion of the fluid if the device, portions of the device, or tissue of the subject reaches an undesired temperature (or a temperature for an undesired period of time).

The present invention is not limited by the type of device or the uses employed. Indeed, the devices may be configured in any desired manner. Likewise, the systems and devices may be used in any application where energy is to be delivered. Such uses include any and all medical, veterinary, and research applications. However, the systems and devices of the present invention may be used in agricultural settings, manufacturing settings, mechanical settings, or any other application where energy is to be delivered.

The device is not limited to delivering a particular type of energy. In some embodiments, the type of energy delivered by the device is microwave energy, in other embodiments the type of energy is radio frequency energy while in other embodiments it is multiple types of energy. In some embodiments, the device is combined with other medical devices such as cutting devices. The cutting devices may also employ energy, such as laser or radiofrequency energy.

In some embodiments, the device is configured for percutaneous, laparoscopic, intravascular, intracardiac, or surgical delivery of energy. In some embodiments, the device is configured for delivery of energy to a target tissue or region. The present invention is not limited by the nature of the target tissue or region. Uses include, but are not limited to, treatment of heart arrhythmia, tumor ablation (benign and malignant), control of bleeding during surgery, after trauma, for any other control of bleeding, removal of soft tissue, tissue resection and harvest, treatment of varicose veins, intraluminal tissue ablation (e.g., to treat esophageal pathologies such as Barrett's Esophagus and esophageal adenocarcinoma), treatment of bony tumors, normal bone, and benign bony conditions, intraocular uses, uses in cosmetic surgery, treatment of pathologies of the central nervous system including brain tumors and electrical disturbances, and cauterization of blood vessels or tissue for any purposes. In some embodiments, the surgical application comprises ablation therapy (e.g., to achieve coagulation necrosis). In some embodiments, the surgical application comprises tumor ablation to target, for example, metastatic tumors. In some embodiments, the device is configured for movement and positioning, with minimal damage to the tissue or organism, at any desired location, including but not limited to, the brain, neck, chest, abdomen, and pelvis. In some embodiments, the device is configured for guided delivery, for example, by computerized tomography, ultrasound, magnetic resonance imaging, fluoroscopy, and the like.

The device is not limited to a particular type of coaxial transmission line. In some embodiments, the coaxial transmission line has an inner conductor, a dielectric element, and an outer shield (e.g., outer conductor). In some embodiments, transmission line has a triaxial configuration and has therein a middle coaxial shield (which can be, for example, a metallic foil, film, mesh, or spiral conductor) positioned between the dielectric element and the outer conductor. In some embodiments, the outer shield is a 20-gauge needle or a component of similar diameter to a 20-gauge needle. Preferably, the outer shield is not larger than a 16-gauge needle (e.g., no larger than an 18-gauge needle). In some embodiments, the outer shield is a 17-gauge needle. However, in some embodiments, larger devices are used, as desired. For example, in some embodiments, a 12-gauge diameter is used. The present invention is not limited by the size of the outer shield component. In some embodiments, the center conductor is configured to extend beyond the outer shield for purposes of delivering energy to a desired location. In preferred embodiments, some or all of the feedline characteristic impedance is optimized for minimum power dissipation, irrespective of the type of antenna that terminates at its distal end.

In some embodiments, the systems of the present invention provide multiple feedlines and/or multiple antennas to affect one or more locations in a subject. Such application include, but are not limited to, treating large tumor masses or tumor masses having irregular shapes, where one or more of the components capable of delivered energy is inserted to a first position of a tumor and one or more of the components is inserted to a second (third, etc.) position of a tumor. In some embodiments, a first component capable of delivering energy is a first size and a second component capable of delivery energy is a second size. Such an embodiment, adds to the choices a user has in delivering the desired amount of energy for a particular application. For example, in embodiments where the size of the injury created by insertion of the device into a subject is less relevant and the tissue zone to be ablated is larger, the user may select a larger needle to deliver more energy. In contrast, where the injury associated with the insertion is to be minimized, two or more smaller needles may be used (e.g., bundled together or separately). In preferred embodiments, some or all of the feedline characteristic impedance is optimized for minimum power dissipation, irrespective of the type of antenna that terminates its distal end. In some embodiments, the device has therein multiple antenna arrays of the same or different shapes (e.g., umbrella-shaped probes, trident shaped, etc.).

In some embodiments, one or more components of the systems of the present invention may contain a coating (e.g., Teflon or any other insulator) to help reduce heating or to impart other desired properties to the component or system. For example, in some embodiments of the present invention, the antennae, and or the feedline, are coated with a biocompatible material that reduces tissue sticking to the device (e.g., Teflon). Coating prevents undesired tissue sticking during use of the device, and thereby permits the antennae to be used without additional cooling measures (e.g., the antennae may be used without having coolant directly engaging the antennae).

In some embodiments, the device further comprises a tuning element for adjusting the amount of energy delivered to the tissue region. In some embodiments, the tuning element is manually adjusted by a user of the system. In some embodiments, the device is pretuned to the desired tissue and is fixed throughout the procedure. In some embodiments, the tuning element is automatically adjusted and controlled by a processor of the present invention. In some embodiments, the processor adjusts the energy delivery over time to provide constant energy throughout a procedure, taking into account any number of desired factors including, but not limited to, heat, nature and/or location of target tissue, size of lesion desired, length of treatment time, proximity to sensitive organ areas, and the like. In some embodiments, the system comprises a sensor that provides feedback to the user or to a processor that monitors the function of the device continuously or at time points. The sensor may record and/or report back any number of properties, including, but not limited to, heat at one or more positions of a components of the system, heat at the tissue, property of the tissue, and the like. The sensor may be in the form of an imaging device such as CT, ultrasound, magnetic resonance imaging, or any other imaging device. In some embodiments, particularly for research application, the system records and stores the information for use in future optimization of the system generally and/or for optimization of energy delivery under particular conditions (e.g., patient type, tissue type, size and shape of target region, location of target region, etc.).

In certain embodiments, the present invention provides systems for ablation therapy, comprising a power distributor and a device of the present invention for percutaneous delivery of energy to a tissue region. In some embodiments, the power distributor includes a power splitter configured to deliver energy to multiple antennas (e.g., the same energy power to each antenna, different energy powers to different antennas). In some embodiments, the power splitter is able to receive power from one or more power distributors.

In certain embodiments, the present invention provides methods for treating a tissue region, comprising providing a target tissue or organism and a device of the present invention for delivery of energy to a tissue region. In such embodiments, the method further comprises the positioning of the device in the vicinity of the tissue region, and the percutaneous delivering of an amount of energy with the device to the tissue region. In some embodiments, the delivering of the energy results in, for example, the ablation of the tissue region and/or thrombosis of a blood vessel, and/or electroporation of a tissue region. In some embodiments, the tissue region is a tumor. In some embodiments, the tissue region comprises one or more of the heart, liver, genitalia, stomach, lung, large intestine, small intestine, brain, neck, bone, kidney, muscle, tendon, blood vessel, prostate, bladder, and spinal cord.

The systems, devices, and methods of the present invention may be used in conjunction with other systems, device, and methods. For example, the systems, devices, and methods of the present invention may be used with other ablation devices, other medical devices, diagnostic methods and reagents, imaging methods and reagents, and therapeutic methods and agents. Use may be concurrent or may occur before or after another intervention. The present invention contemplates the use systems, devices, and methods of the present invention in conjunction with any other medical interventions.

BRIEF DESCRIPTION OF THE DRAWINGS

FIG. 1A-C shows a transverse cross-section schematic of a standard coaxial cable (100) and two embodiments of the present invention (200, 300).

DETAILED DESCRIPTION

Figure 2:
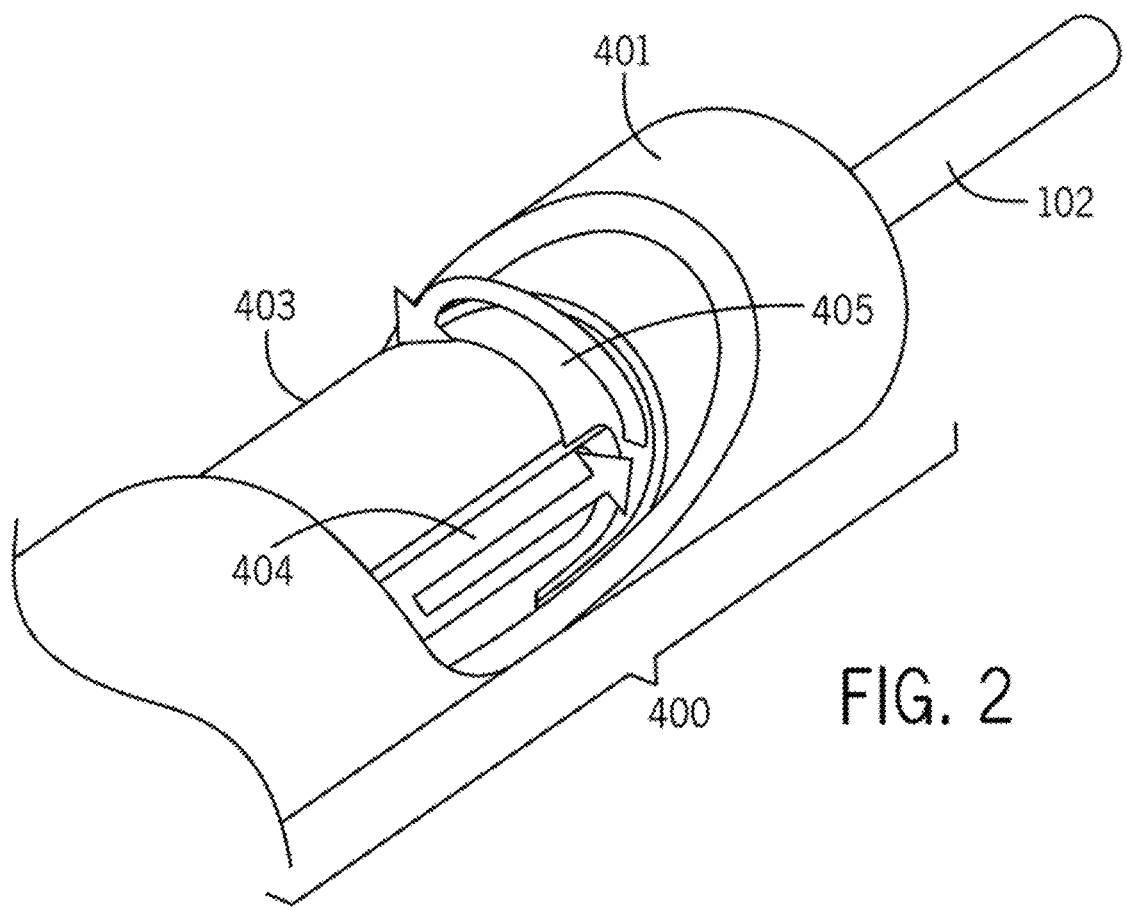
FIG. 2 shows an embodiment of the present invention where longitudinal fluid channels run the length of the cable to the feed point of the antenna, wherein a small transverse channel is inserted to allow fluid flow back through a different channel.

The present invention relates to systems and devices for delivering energy to tissue for a wide variety of applications, including medical procedures (e.g., tissue ablation, treatment of arrhythmias, cautery, vascular thrombosis, electrosurgery, tissue harvest, etc.). In particular, the present invention relates to systems and devices for the delivery of energy with heat transfer ability. In some embodiments, the systems and devices also have variable characteristic impedance as a result of the use of heat transfer materials. In certain embodiments, methods are provided for treating a tissue region (e.g., a tumor) through application of energy with the systems and devices of the present invention.

In preferred embodiments, the systems, devices, and methods of the present invention employ microwave energy. The use of microwave energy in the ablation of tissue has numerous advantages. For example, microwaves have a broad field of power density (e.g., approximately 2 cm surrounding an antenna depending on the wavelength of the applied energy) with a correspondingly large zone of active heating, thereby allowing uniform tissue ablation both within a targeted zone and in perivascular regions (see, e.g., International Publication No. WO 2006/004585; herein incorporated by reference in its entirety). In addition, microwave energy has the ability to ablate large or multiple zones of tissue using multiple probes with more rapid tissue heating. Microwave energy has an ability to penetrate tissue to create deep lesions with less surface heating. Energy delivery times are shorter than with radiofrequency energy and probes can heat tissue sufficiently to create an even and symmetrical lesion of predictable and controllable depth. Microwave energy is generally safe when used near vessels. Also, microwaves do not rely on electrical conduction; they can radiate through tissue, fluid/blood, as well as air. Therefore, they can be used in tissue, lumens, lungs, and intravascularly.

The illustrated embodiments provided below describe the systems and devices of the present invention in terms of medical applications (e.g., ablation of tissue through delivery of microwave energy). However, it should be appreciated that the systems and devices of the present invention are not limited to a medical applications. In addition, the illustrated embodiments describe the systems and devices of the present invention in terms of medical devices configured for tissue ablation. It should be appreciated that the systems and devices of the present invention are not limited to medical devices configured for tissue ablation. The illustrated embodiments describe the systems and devices of the present invention in terms of microwave energy. It should be appreciated that the systems and devices of the present invention are not limited to a particular type of energy (e.g., radiofrequency energy).

The systems and devices of the present invention provide numerous advantages over the currently available systems and devices. For example, a major drawback with currently available medical devices that utilize microwave energy is the undesired dissipation of the energy through transmission lines onto a subject's tissue resulting in undesired burning. Such microwave energy loss results from limitations within the design of currently available medical devices. In particular, medical devices utilizing microwave energy transmit energy through coaxial cables having therein a dielectric material (e.g., polyfluorothetraethylene or PTFE) surrounding an inner conductor. Dielectric materials such as PTFE have a finite conductivity, which result in the undesired heating of transmission lines. This is particularly true when one supplies the necessary amounts of energy for a sufficient period of time to enable tissue ablation. The present invention provides systems, devices, and methods that overcome this limitation. In particular, the present invention provides means for flowing coolant through the device to manage heating. As described in more detail below, the overall temperature of the transmission lines within the medical devices of the present invention are reduced, and therefore, reduces undesired tissue heating. Thus, in some embodiments, the systems and devices of the present invention are provided with a coolant that runs through at least a portion of the dielectric material, which may be partly or completely made of mesh or other porous construction. This is in contrast, for example, to coolant systems that are provided in an external cooling jacket that surrounds a coaxial cable, antenna, or device.

In addition, in some embodiments, by providing improved coaxial transmission lines configured for coolant material circulation, by using one or more space-saving techniques, the coaxial transmission line may be designed such that it can fit within very small needles (e.g., 16-20 gauge needles or smaller). Typically, medical devices configured to delivery microwave energy are designed to fit within large needles due to bulky dielectric materials. Microwave ablation has not been extensively applied clinically due to the large probe size (14 gauge) and relatively small zone of necrosis (1.6 cm in diameter) (Seki T et al., Cancer 74:817 (1994)) that is created by the only commercial device (Microtaze, Nippon Shoji, Osaka, Japan. 2.450 MHz, 1.6 mm diameter probe, 70 W for 60 seconds). Other devices use a cooling external water jacket that also increases probe size and can increase tissue damage. These large probe sizes increase the risk of complications when used in the chest and abdomen. In some embodiments of the present invention, the maximum outer diameter of the portion of the device that enters a subject is 16-18 gauge or less (20 gauge or less).

Moreover, by providing improved coaxial transmission lines designed to prevent undesired heating, the coaxial cables may be heated to temperatures at or above (e.g., 10%, 20%, 50%, etc. above) the manufacturer's rated temperature failure points.

The energy delivery systems of the present invention contemplate the use of any type of device configured to deliver (e.g., emit) energy (e.g., ablation device, surgical device, etc.) (see, e.g., U.S. Pat. Nos. 7,101,369, 7,033,352, 6,893,436, 6,878,147, 6,823,218, 6,817,999, 6,635,055, 6,471,696, 6,383,182, 6,312,427, 6,287,302, 6,277,113, 6,251,128, 6,245,062, 6,026,331, 6,016,811, 5,810,803, 5,800,494, 5,788,692, 5,405,346, 4,494,539, U.S. patent application Ser. Nos. 11/514,628, 11/502,783, 11/452,637, 11/440,331, 11,237,430, 11/237,136, 11/236,985, 10/980,699, 10/961,994, 10/961,761, 10/834,802, 10/370,179, 09/847,181; U.S. Provisional Patent Nos. 60/785,690, 60/785,467, and 60/785,466; Great Britain Patent Application Nos. 2,406,521, 2,388,039; European Patent No. 1395190; and International Patent Application Nos. WO 06/008481, WO 06/002943, WO 05/034783, WO 04/112628, WO 04/033039, WO 04/026122, WO 03/088858, WO 03/039385 WO 95/04385; each herein incorporated by reference in their entireties). Such devices include any and all medical, veterinary, and research applications devices configured for energy emission, as well as devices used in agricultural settings, manufacturing settings, mechanical settings, or any other application where energy is to be delivered.

In some embodiments, the systems utilize energy delivery devices having therein antennae configured to emit energy (e.g., microwave energy, radiofrequency energy). The systems are not limited to particular types or designs of antennae (e.g., ablation device, surgical device, etc.). In some embodiments, the systems utilize energy delivery devices having linearly shaped antennae (see, e.g., U.S. Pat. Nos. 6,878,147, 4,494,539, U.S. patent application Ser. Nos. 10/961,994, 10/961,761; U.S. Provisional Patent Nos. 60/785,690, 60/785,467, and 60/785,466; and International Patent Application No., WO 03/039385; each herein incorporated by reference in their entireties). In some embodiments, the systems utilize energy delivery devices having non-linearly shaped antennae (see, e.g., U.S. Pat. Nos. 6,251,128, 6,016,811, and 5,800,494, U.S. patent application Ser. No. 09/847,181, and International Patent Application No. WO 03/088858; each herein incorporated by reference in their entireties). In some embodiments, the antennae have horn reflection components (see, e.g., U.S. Pat. Nos. 6,527,768, 6,287,302; each herein incorporated by reference in their entireties). In some embodiments, the antenna has a directional reflection shield (see, e.g., U.S. Pat. No. 6,312,427; herein incorporated by reference in its entirety). In some embodiments, the antenna has therein a securing component so as to secure the energy delivery device within a particular tissue region (see, e.g., U.S. Pat. Nos. 6,364,876, and 5,741,249; each herein incorporated by reference in their entireties).

The energy emitting devices of embodiments of the present invention may be manufactured in a variety of ways. An exemplary manufacturing method for a triaxial device of some embodiments of the invention is provided below. In some embodiments, an interior portion comprising the inner conductor is made first. In some such embodiments, a inner conductor is provide and is coated with a dielectric material and a thin metal coating. In some embodiments, no dielectric material is used (e.g., air or other material occupies the space between the inner conductor and the thin metal coating). In some embodiments, the thin metal coating is a metal foil that is wrapped around the inner conductor and/or dielectric material. In some embodiments, the dielectric material and metal coating are provided by use of a metal-coated deformable tube (e.g., Kapton tube) that is inserted over the inner conductor. One or more of the components may be glued to one another. In some embodiments, this assembly is manufactured in long lengths that are cut to size. In other embodiments, the assembly is manufactured at final length. In some embodiments, coolant tubes (e.g., deformable tubes) are then attached to the outer surface of the conductive metal or film. The coolant tubes may run any desired length along the device. This assembly may also be manufactured in long lengths and cut to size. An outer conductor is then placed over the assembly, encompassing the inner conductor, the metal film or foil, and the coolant tubes. In some embodiments, the inner conductor extends distally beyond the length of the other components. This portion of the inner conductor may be covered in a non-conductive material, so as to provide an antenna for energy delivery. In some embodiments, a non-conducive tip is positioned on the distal end of the device. The tip may be fashioned with a sharp point to assist in penetration of and navigation through tissue. In some embodiments, a handle is positioned on the proximal end of the device. In some embodiments, the handle is provided as two or more pieces that snap or are fused together. The handle pieces contain channels to accommodate an electric connection between the triaxial cable a power delivery system and between a coolant source and coolant tubes or channels in the energy delivery device. In some embodiments, connections are sealed. In some embodiments, one or more of the tip, antenna portion, feed line portion (comprising the triaxial cable), and handle are coated with a material that provides one or more of: biocompatibility and non-stick surface. Non-conductive segments may be attached to metal coated segments via any desired mechanism. In some embodiments, connections are designed to "snap fit" into a secure engagement, for example, at the end of the triaxial cable. In some embodiments, glue or other adhesives are used. In some embodiments, insert molding/thermoforming is used. For example, holes may be drilled in the end of the outer conductor of the triaxial cable and insert molding/thermoforming is carried out by melting the non-conductive material so that it forms into the holes.

The present invention is not limited to a particular coaxial transmission line cross-sectional shape. Indeed, in some embodiments, the shape of the coaxial transmission line and/or the dielectric element is selected and/or adjustable to fit a particular need. For example, potential cross-sectional shapes for the transmission lines or portions thereof (e.g., at the circumference of the dielectric material, the middle coaxial shield, the outer conductor, etc.). include, but are not limited to, circular, oval, square, rectangular, oblong, diagonal, triangular, or various irregular shapes. In some embodiments, the shapes are designed so as to accommodate and/or include flow channels within the transmission line. In some embodiments, the transmission line is shaped to assume a particular region of interest (e.g., a body orifice). Certain preferred embodiments of the present invention are described below. The present invention is not limited to these embodiments.

FIG. 1A-C shows a conventional coaxial cable 100 and two exemplary cables of the present invention, 200 and 300. A coaxial cable is made, generally, of three separate spaces: a metallic inner conductor 110, a metallic outer conductor 130, and a space between them. The space between them is usually filled with a low-loss dielectric material 120 (e.g., polyfluorotetraethylene, or PTFE) to mechanically support the inner conductor and maintain it with the outer conductor. The characteristic impedance of a coaxial cable is fixed by the ratio of diameters of the inner conductor and dielectric material (i.e., inner diameter of the outer conductor) and the permittivity of the space between them. Usually, the permittivity is fixed because of the solid polymer comprising it. However, in embodiments of the present invention, a fluid with variable permittivity (or conductivity) at least partially occupies this space, permitting the characteristic impedance of the cable to be adjusted.

In one embodiment of the present invention, the coaxial cable 200 has the outer portion of the dielectric material removed to create a channel between the dielectric material 120 and the outer conductor 130. In the embodiments shown, the created space is separated into four distinct channels 150 by the addition of support lines 140 configured to maintain the space between the outer conductor 130 and the solid dielectric material 120. The support lines 140 may be made of any desired material and may be the same or a different material as the solid dielectric material 120. The presence of multiple channels permits one or more of the channels to permit flow in one direction (towards the proximal end of the cable) and one or more other channels to permit flow in the opposite direction (towards the distal end of the cable).

In another embodiment, the coaxial cable 300 has a substantial portion of the solid dielectric material 120 removed. Such an embodiment may be generated, for example, by stripping away the solid dielectric material 120 down to the surface of inner conductor 110 on each of four sides. In another embodiment, strips of dielectric material 120 are applied to an inner conductor 110 to create the structure. In this embodiment, four channels 150 are created. By removing a substantial amount of the dielectric material 120, the diameter of the outer conductor 130 is substantially reduced. The corners provided by the remaining dielectric material 120 provide the support to maintain the position of the outer conductor 130 with respect to the inner conductor 110. In this embodiment, the overall diameter of the coaxial cable 300 and the device is substantially reduced.

Large electric fields caused by large powers and small cable diameters can generate heat within the dielectric material that lead to unwanted heating of the medium (e.g., tissue) into which the cable is immersed. Thus, it is desirable to be able to counteract this effect and sink heat out of the cable to reduce any unwanted heating. The present invention provides devices configured to circulate coolant materials for purposes of sinking heat away from the cable itself, and thereby reducing unwanted heating of the medium (e.g., tissue).

Figure 3:
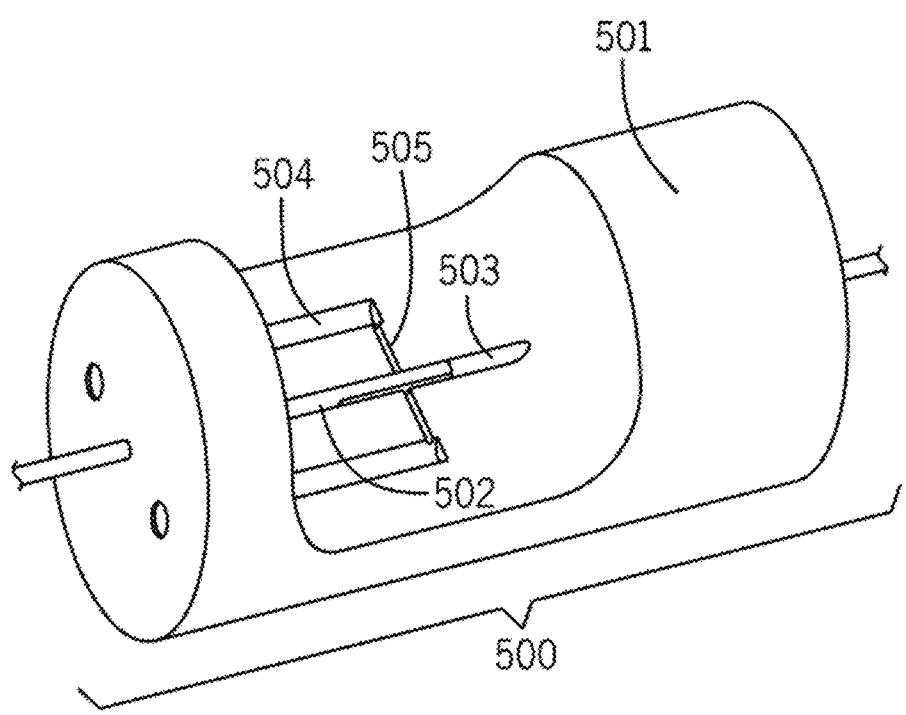
FIG. 3 shows an embodiment of a device of the present invention to flow fluid to and from the cable.

The present invention is not limited by the nature of the coolant material employed. Coolants included, but are not limited to, liquids and gasses. Exemplary coolant fluids include, but are not limited to, one or more of or combinations of, water, glycol, air, inert gasses, carbon dioxide, nitrogen, helium, sulfur hexafluoride, ionic solutions (e.g., sodium chloride with or without potassium and other ions), dextrose in water, Ringer's lactate, organic chemical solutions (e.g., ethylene glycol, diethylene glycol, or propylene glycol), oils (e.g., mineral oils, silicone oils, fluorocarbon oils), liquid metals, freons, halomethanes, liquified propane, other haloalkanes, anhydrous ammonia, sulfur dioxide. In some embodiments, cooling occurs, at least in part, by changing concentrations of coolant, pressure, or volume. For example, cooling can be achieved via gas coolants using the Joule-Thompson effect. In some embodiments, the cooling is provided by a chemical reaction. The devices are not limited to a particular type of temperature reducing chemical reaction. In some embodiments, the temperature reducing chemical reaction is an endothermic reaction. The devices are not limited to a particular manner of applying endothermic reactions for purposes of preventing undesired heating. In some embodiments, first and second chemicals are flowed into the device such that they react to reduce the temperature of the device. In some embodiments, the device is prepared with the first and second chemicals preloaded in the device. In some embodiments, the chemicals are separated by a barrier that is removed when desired. In some embodiments, the barrier is configured to melt upon exposure to a predetermined temperature or temperature range. In such embodiments, the device initiates the endothermic reaction only upon reaching a heat level that merits cooling. In some embodiments, multiple different barriers are located throughout the device such that local cooling occurs only at those portions of the device where undesired heating is occurring. In some embodiment, the barriers used are beads that encompass one of the two chemicals. In some embodiments, the barriers are walls (e.g., discs in the shape of washers) that melt to combine the two chemicals. In some embodiments, the barriers are made of wax that is configured to melt at a predetermined temperature. The devices are not limited to a particular type, kind or amount of meltable material. In some embodiments, the meltable material is biocompatible. The devices are not limited to a particular type, kind, or amount of first and second chemicals, so long as their mixture results in a temperature reducing chemical reaction. In some embodiments, the first material includes barium hydroxide octahydrate crystals and the second material is dry ammonium chloride. In some embodiments, the first material is water and the second material is ammonium chloride. In some embodiments, the first material is thionyl chloride ($SOCl_2$) and the second material is cobalt(II) sulfate heptahydrate. In some embodiments, the first material is water and the second material is ammonium nitrate. In some embodiments, the first material is water and the second material is potassium chloride. In some embodiments, the first material is ethanoic acid and the second material is sodium carbonate. In some embodiments, a meltable material is used that, itself, reduces heat by melting an flowing in a manner such that the heat at the outer surface of the device is reduced. FIGS. 2, 3, and 7 show device embodiments configured to provide this benefit.

FIG. 2 shows a coaxial cable 400 comprising an outer conductor 401, and an inner conductor 402 that may be extended from the end of the device to deliver energy to a target tissue. The solid dielectric material 403 has a channel carved therein 404 that permits fluid flow down the longitudinal length of the coaxial cable 400 to the feed point of the antenna. In this embodiment, a small transverse channel 405 is provided to allow fluid flow back through a different channel (not shown). In some embodiments, a fluid reservoir is provided instead of the small transverse channel. A fluid reservoir can be created, for example, by removing the dielectric material of the coaxial cable at the location where the cooling channel terminates.

FIG. 3 shows a cut-away view of a coaxial cable 500 with an inner conductor 502 covered by a coating 503 contained within a solid dielectric material 501. Two channels 504 are cut through the interior of the dielectric material 501 to permit flow of fluid. A small transverse channel 505 is provided to allow fluid flow between the two channels.

Figure 7A:
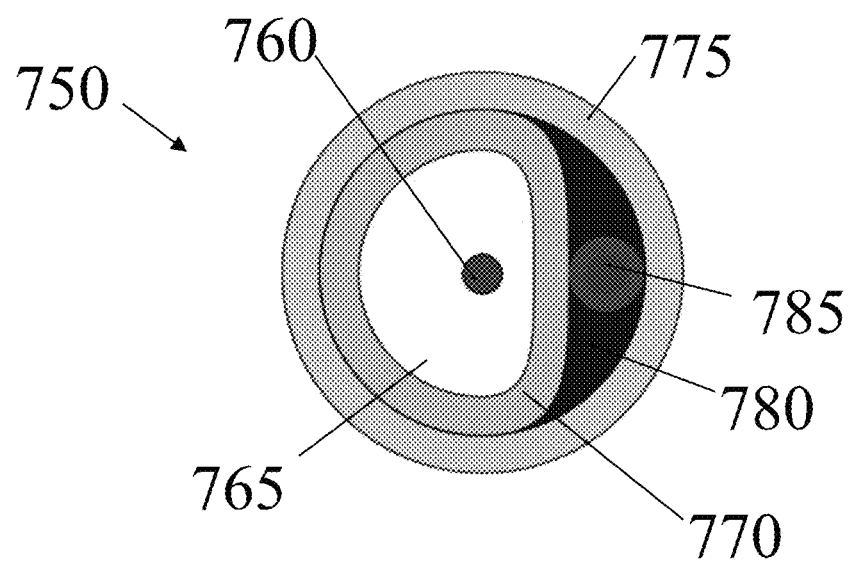
FIG. 7A-F show a series of cross-sectional views of cables having an inner conductor, a dielectric material, a middle coaxial shield, and an outer conductor, in some embodiments of the present invention.
Figure 7B:
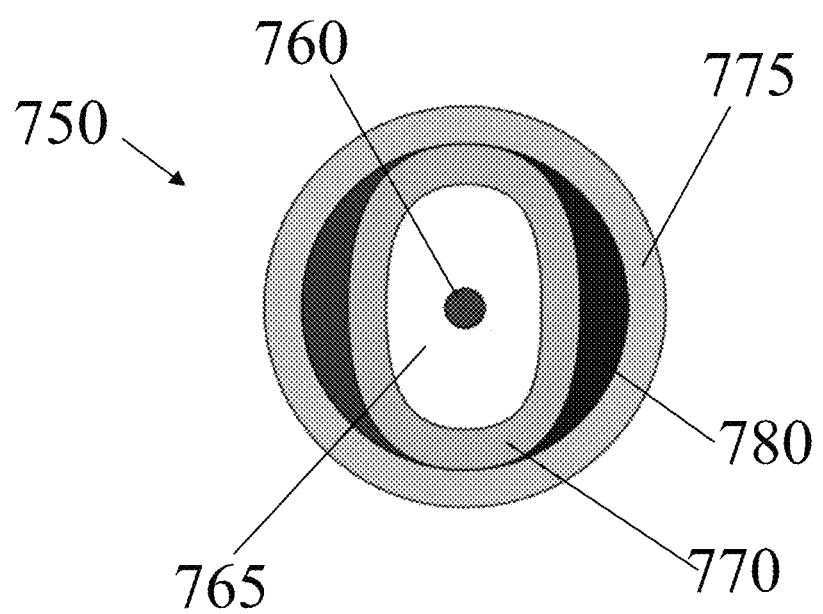
Figure 7C:
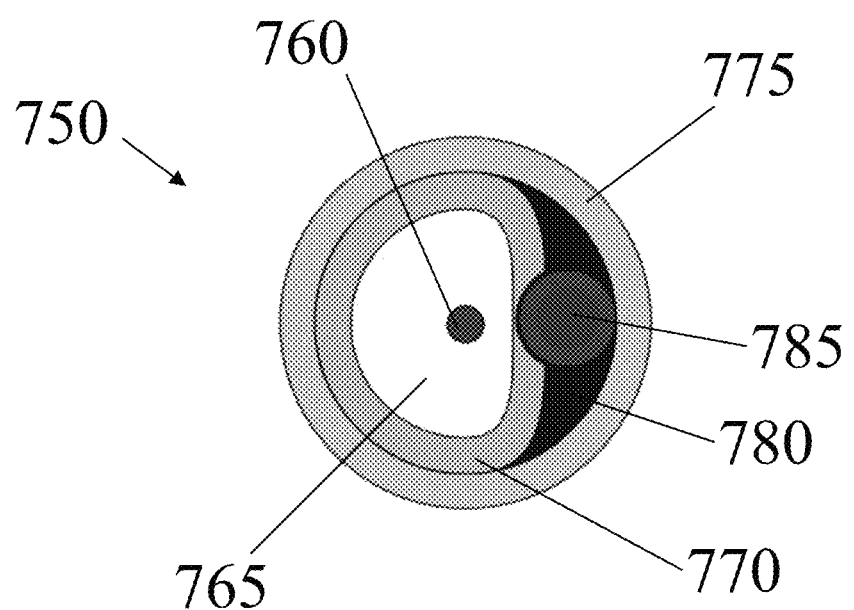
Figure 7D:
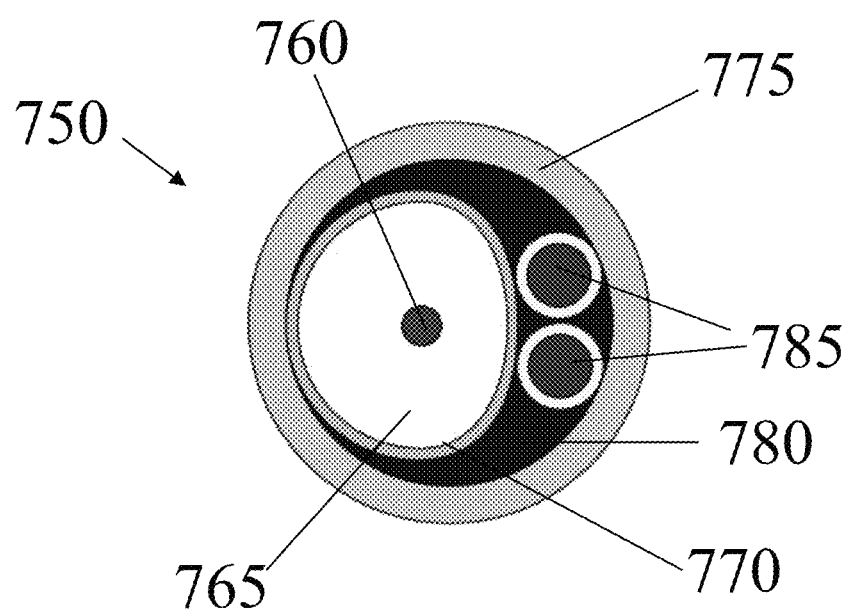
Figure 7E:
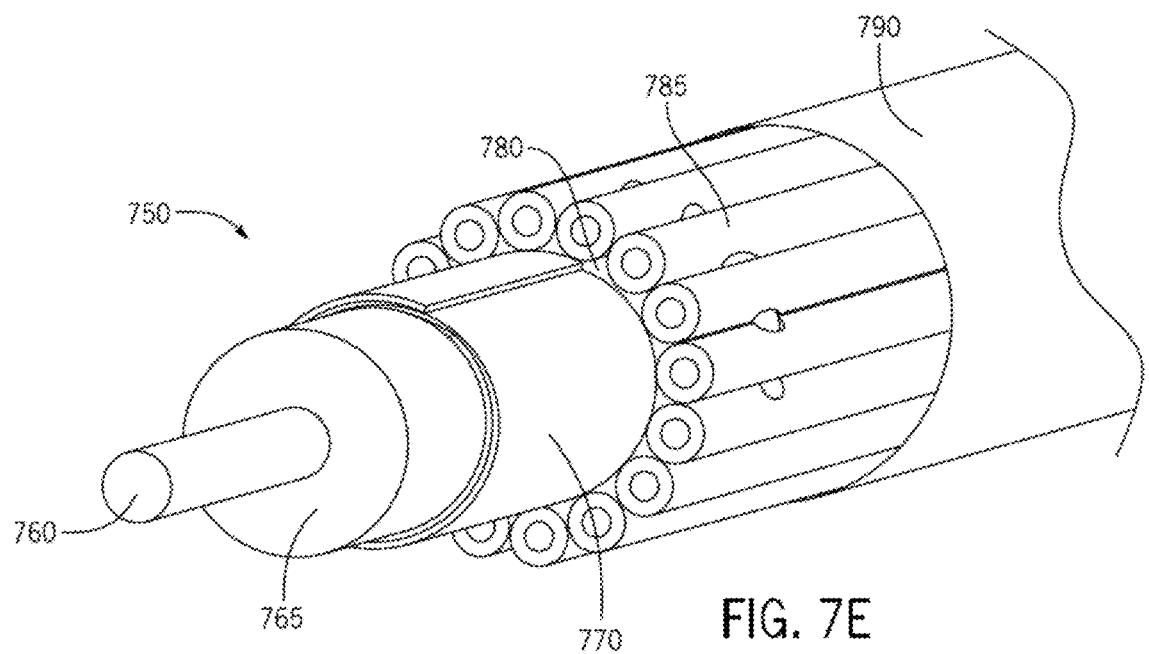
Figure 7F:
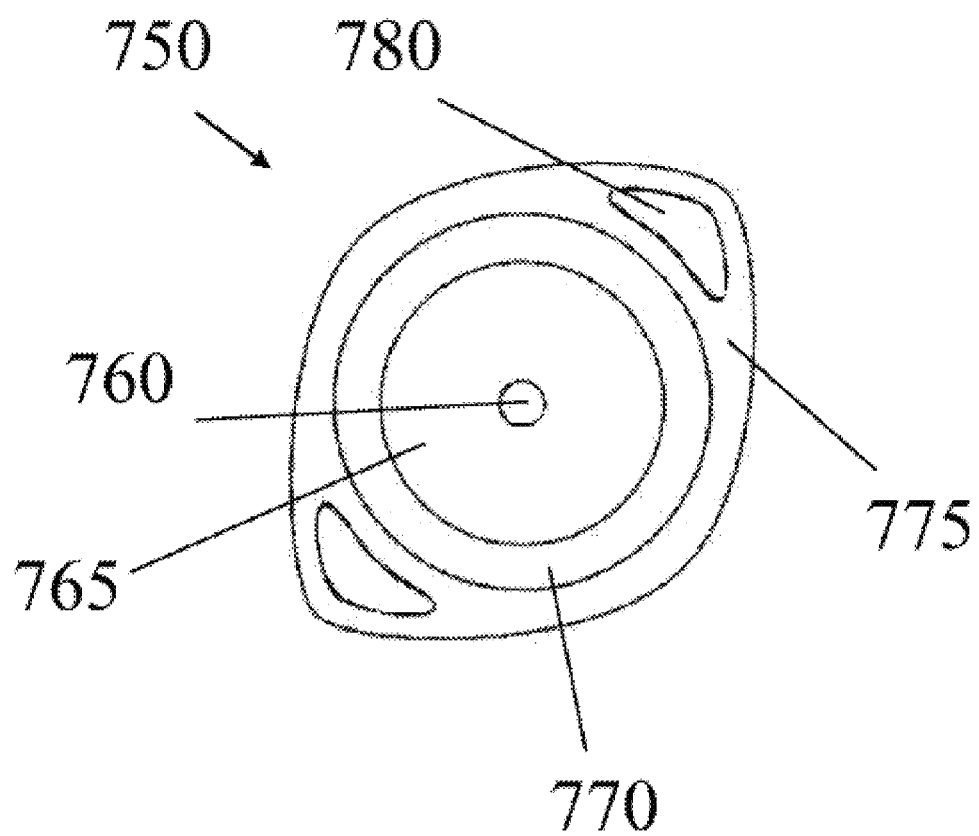

FIGS. 7A-F show a series of cross-sectional views of cables 750 having an inner conductor 760, a dielectric material 765, a middle coaxial shield 770 (shown as a thin film or foil in 7D and E), and an outer conductor 775. FIGS. 7A-E show the coaxial cable 750 having therein gap areas 780 inbetween the middle coaxial shield 770 and the outer conductor 775. FIG. 7F shows the coaxial cable 750 having therein gap areas 780 within the outer conductor 775. In some embodiments, the gap areas 780 may be used for circulating a coolant material. In some embodiments, such a coaxial cable may have only one gap area, while in other embodiments, as shown in FIGS. 7B and 7F, there are two segregated gap areas. Such a configuration as shown in FIGS. 7B and/or 7F permit the input of coolant material through one of the gap areas and the output of the inputted coolant material through the other gap area. Such a configuration as shown in FIG. 7B permits the input of coolant material through one of the gap areas and the output of the inputted coolant material through the other gap area. In some embodiments, channels are created by deforming an otherwise circular assembly comprising an inner conductor, dielectric material and middle coaxial shield. In some embodiments, the channels are created by filling the space between with the coaxial shield and the outer conductor with a material and removing a portion of the material to create a channel. In some embodiments, the material is a curable material and strips of the material are cured by providing heat along the length of the exterior surface of the outer conductor to create thin, cured strips. The uncured material is then removed, to create channels that are separated by the barriers of cured material.

In some embodiments, as shown in FIGS. 7A, C, D and E the coaxial cable 750 has therein at least one coolant tube 785 positioned within the gap areas 780. The present invention is not limited to a particular type or kind of coolant tube 785. In some embodiments, the composition of the coolant tube 785 is metal, plastic, ceramic, Kevlar, etc. In some embodiments, the coolant tube 785 is a deformable tube capable of assuming a variety of shapes and configurations (e.g., a Kapton Tube). In some embodiment, the coolant tube 785 is temperature resistant.

In some embodiments, as shown in FIGS. 7A, D and E, the coolant tube(s) 785 is positioned such that it does not effect the thickness of the middle coaxial shield 770 or the outer conductor 775. In some embodiments, as shown in FIGS. 7C, the coolant tube(s) 785 is positioned such that it encroaches upon the middle coaxial shield 770 thereby reducing the thickness of the middle coaxial shield 770 at the location of encroachment. In some embodiments, the coolant tube(s) is positioned such that it encroaches upon the middle coaxial shield 770 and the outer conductor 775 thereby reducing the thickness of the middle coaxial shield 770 and the outer conductor 775 at the location of encroachment. In some embodiments, the coolant tube(s) is positioned such that it encroaches upon only the outer conductor 775 thereby reducing the thickness of the outer conductor 775 at the location of encroachment.

In some embodiments, as shown in FIGS. 7A and 7C, only one coolant tube 785 is positioned within the gap area 780. In such embodiments, a coolant material may be inputted through the coolant tube 785 and outputted through the gap area 780, or the coolant material inputted through the gap area 780 and outputted through the coolant tube 785.

In some embodiments, as shown in FIG. 7D, two coolant tubes 785 are positioned within the gap area 780. In such embodiments, the coolant material may be inputted through the two coolant tubes 785 and outputted through the gap area 780, or the coolant material inputted through one of the coolant tubes 785 and outputted through the second coolant tube 785, or the coolant material inputted through the gap area 780, and outputted through the coolant tubes 785.

In some embodiments, as shown in FIG. 7E, a plurality of coolant tubes 785 are positioned along the outside of the middle coaxial shield 770. In such embodiments, any number (e.g., 1, 2, 5, 10) of the coolant tubes 785 may be used to input the coolant material and any number (e.g., 1, 2, 5, 10) of the coolant tubes 785 may be used to output the coolant material. In some embodiments, half of the coolant tubes 785 are used to input coolant material and half of the coolant tubes 785 are used to output coolant material. In some embodiments, the gap area 780 may be used to input or output coolant material. In some embodiments, the coolant tubes 785 are conductive and replace the outer conductor. In some embodiments, a thin non-conductive sheath 790 encases the device.

In some embodiments, the coaxial cable prevents unwanted heating along the length of the coaxial cable through the positioning of a plurality of coolant tubes along the exterior of the outer conductor. FIG. 7F provides one such example. In this configuration channels are provided in the out conductor. However, in other embodiments, channels (e.g., tubing) may affixed to the outer surface of the outer conductor. In some such embodiments, the device may be covered in a sheath (e.g., shrink-wrap material) to securely hold the channels to the outside of the outer conductor. These embodiments, may cause the device to take on oval or modified oval shape.

In some embodiments, the device has a handle attached with the device, wherein the handle is configured to, for example, control the passing of coolant into and out of the coolant channels and/or coolant tubes. In some embodiments, the handle is also connected to coolant and energy delivery systems via a one or more cables. In some embodiments, a single cable connects the energy delivery system (e.g., generator) and coolant system to the handle. In some embodiments, the cable is attached to the handle at a 90-degree angle or approximately a 90-degree angle.

In some embodiments, the coolant handling system is provided to manage the flow of coolant to the device. In some embodiments, the coolant handling system is manually controlled. In some embodiments, the coolant handling system is automatically controlled. In some embodiments, the temperature of returning coolant is monitored and the temperature is used to determine flow rate of input coolant. In some embodiments, the energy delivery is also control based on temperature of one or more portions of the device. An automated or partially automated system may control a wide variety of operations. For example, in some embodiments, when the device is ready for operation, the automated system primes the cooling system by circulating coolant or another material through the coolant passageways. Once the system is primed, the program enters a normal coolant management protocol. In some embodiments, one or more temperature sensors that monitor temperature of the coolant, one or more portions of the device, or the surrounding tissue, are used to control coolant flow and/or energy delivery. For example, in some embodiments, the temperature of the tip or antenna is monitored to make sure it is sufficiently high (e.g., before starting a procedure or before activating the energy delivery mode), while the temperature of the feed line or handle is monitored to maintain a portion of the device at sufficiently low temperature to avoid tissue damage proximal to the treated region.

The impedance of the device connected to the end of the coaxial cable can also be variable. There are many instances for which this is true, including: a device whose input impedance changes with temperature (e.g., a resonant antenna in a medium of changing permittivity, as in microwave ablation), whose impedance changes over time, changed based on loading further downstream in the network, etc. In these instances, it may be beneficial to change the impedance of the coaxial line feeding these devices. For example, a microwave ablation antenna at the end of a coaxial cable may resonate inside the tissue at an initial temperature, $T_0$. As the tissue warms, the input impedance and, thus, the resonant frequency of the antenna shift along with the dielectric properties of the tissue. This shift causes an impedance mismatch between the feeding coaxial cable and the antenna, which results in reflections from the antenna. This, in turn, results in reduced efficiency in the antenna, less of the desired tissue heating effect and more of the undesirable heating of the feed cable and peripheral tissue proximal to the antenna.

However, if the characteristic impedance of the cable is adjusted to continuously match the antenna, then lower reflections and less of the undesirable feed cable heating would occur. The present invention provides means for providing this matching by altering the fluid passed through the channels to adjust the characteristic impedance. The present invention also provides means for reducing the undesired heating by flowing coolant though the channels.

Figure 4:
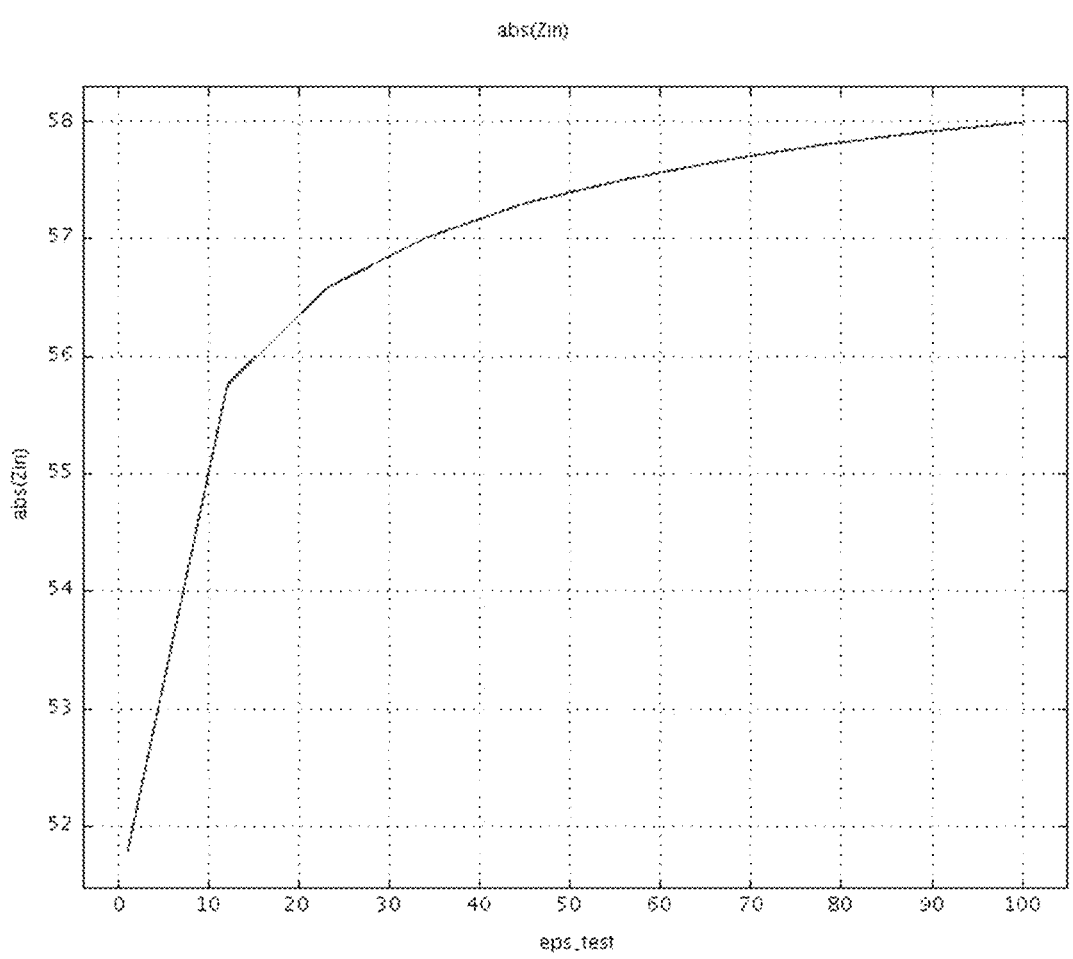
FIG. 4 shows a graph of characteristic impedance of a simulated line versus relative permittivity of the fluid layer.
Figure 5:
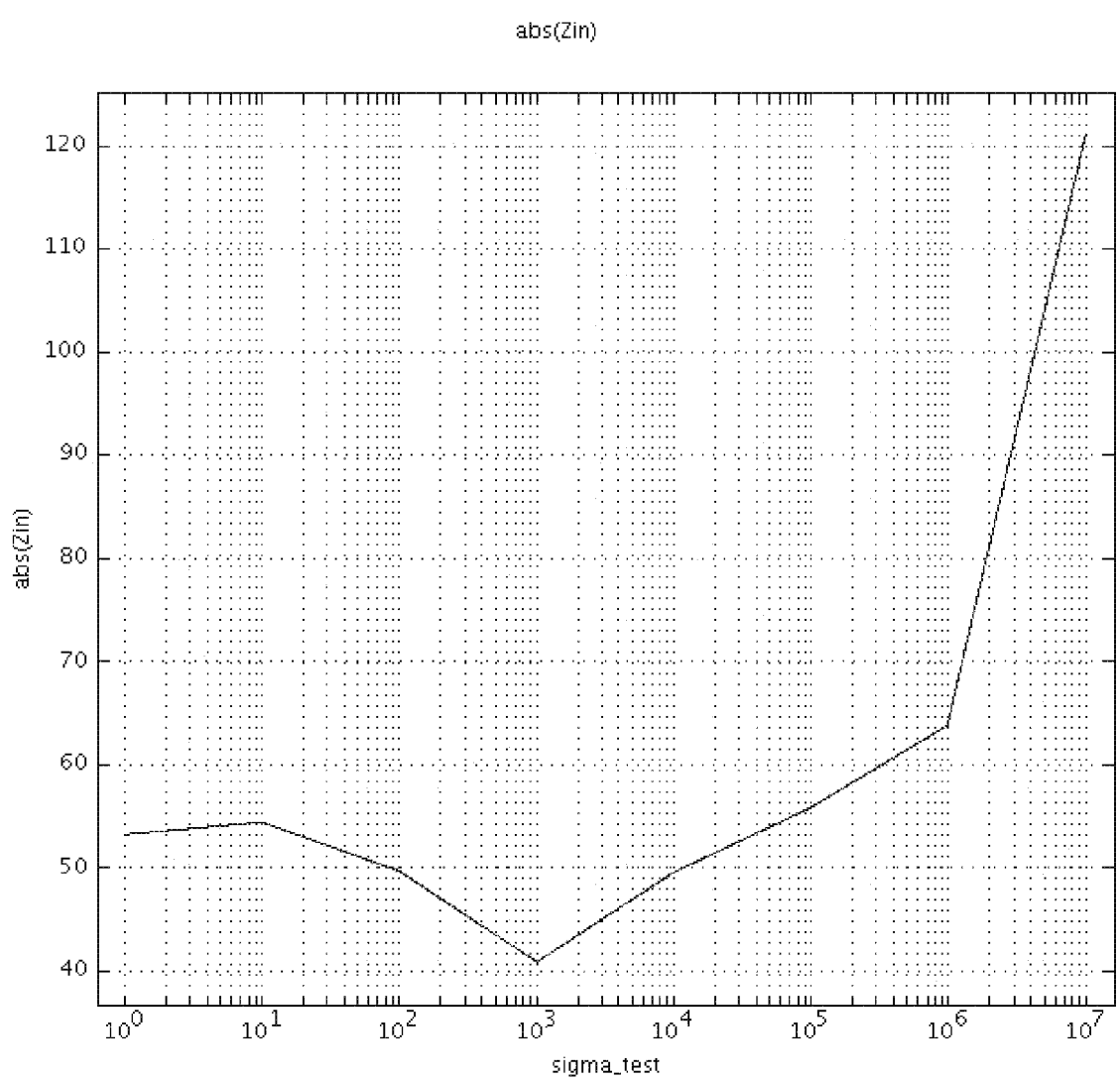
FIG. 5 shows a graph of characteristic impedance versus conductivity of the fluid layer.
Figure 6A:
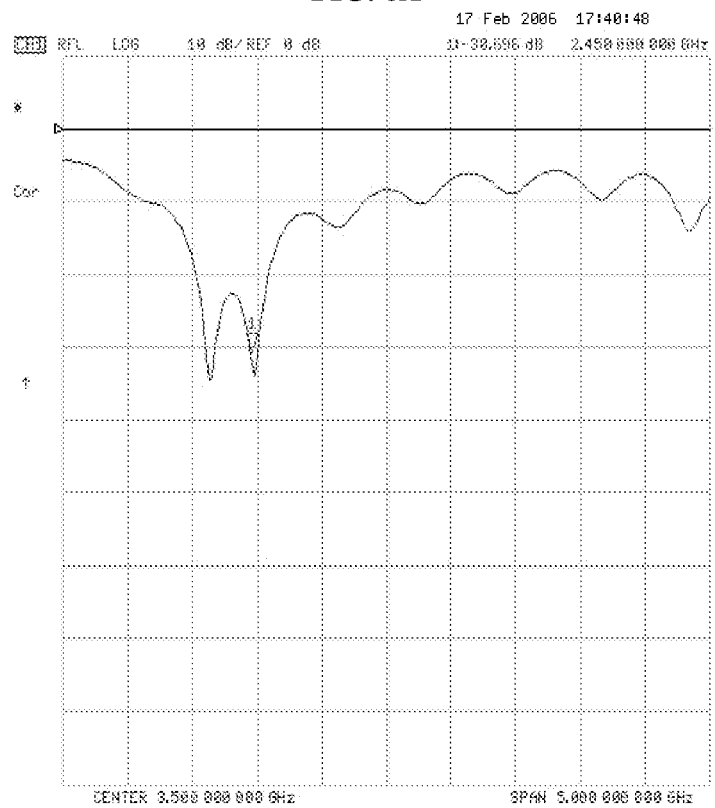
FIG. 6A-B shows graphs of reflection coefficient versus frequency for a triaxial antenna with standard coaxial cable (FIG. 6A) and the same antenna fed by a water-filled cable (FIG. 6B).
Figure 6B:
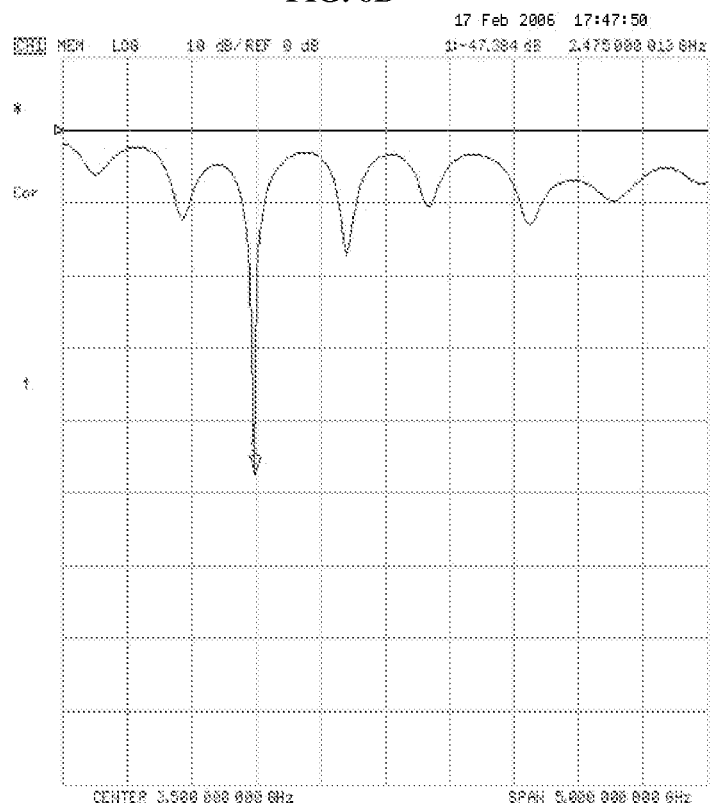

Experiments conducted in the development of embodiments for the present invention simulated and experimentally generated results to demonstrate this effect. In the simulations, a 0.1 mm layer of fluid was assumed to flow between the outer surface of the dielectric layer and the inner surface of the outer conductor. When the relative permittivity of this medium changes from 1-100, the characteristic impedance changes slightly (FIG. 4). FIG. 4 shows a graph of characteristic impedance of a simulated line versus relative permittivity of the fluid layer. The rest of the dielectric core was assumed to be PTFE (eps_r=1.8). Similarly, when the conductivity of the fluid layer is altered, larger changes in impedance can be observed (FIG. 5). FIG. 5 shows a graph of characteristic impedance versus conductivity of the fluid layer. Relative permittivity was assumed to be 1.8 in the fluid layer. A thicker fluid layer would result in more drastic changes in characteristic impedance. Experimental results show that not only is such a cable feasible, but the cable does not degrade (and may have improved) the reflection coefficient of the antenna. FIG. 6A-B shows the reflection coefficient versus frequency for a triaxial antenna with standard coaxial cable (top) and the same antenna fed by a water-filled cable (bottom).

The systems and devices of the present invention may be combined within various system/kit embodiments. For example, the present invention provides kits comprising one or more of a generator, a power distribution system, and an applicator device, along with any one or more accessory agents (e.g., surgical instruments, software for assisting in procedure, processors, temperature monitoring devices, etc.). The present invention is not limited to any particular accessory agent. Additionally, the present invention contemplates kits comprising instructions (e.g., ablation instructions, pharmaceutical instructions) along with the systems and devices of the present invention and/or a pharmaceutical agent (e.g., a sedating medication, a topical antiseptic, a topical anesthesia).

The devices of the present invention may be used in any medical procedure (e.g., percutaneous or surgical) involving delivery of energy (e.g., microwave energy) to a tissue region. The present invention is not limited to a particular type or kind of tissue region (e.g., brain, liver, heart, blood vessels, foot, lung, bone, etc.). For example, the systems of the present invention find use in ablating tumor regions. In such uses, the applicator device is inserted into, for example, a subject such that the distal end of the distal coaxial outer shield is positioned in the vicinity of the desired tissue region. Next, the generator is used to provide a desired amount of microwave energy to the power distribution system at a characteristic impedance level, which in turn provides the energy at a characteristic impedance level to the applicator device. Next, in some embodiments, through use of a visualizing agent, the distal coaxial center conductor is extended from the distal coaxial outer shield in a manner retaining the characteristic impedance level. Next, a desired amount of microwave energy is delivered to the desired tissue region (e.g., tumor) generating an electric field of sufficient strength to ablate the desired tissue region. Due to the characteristic impedance level maintained throughout the transmission lines of the applicator device, the overall temperature of the transmission lines is greatly reduced, resulting in a reduced chance for undesired tissue overheating. The present invention further provides methods involving the simultaneous use of multiple (e.g., two or more) applicator devices for the treatment of a tissue. The present invention further provides methods involving the simultaneous use of multiple (e.g., two or more) applicator devices for the treatment of a tissue. In some embodiments, the present invention provides methods wherein the simultaneous use of multiple antennas are phased to achieve constructive and destructive interference (e.g., for purposes of selectively destroying and sparing portions of a tissue region).

In some embodiments, the present invention further provides software for regulating the amount of microwave energy provided to a tissue region through monitoring of the temperature of the tissue region (e.g., through a feedback system). In such embodiments, the software is configured to interact with the systems for microwave therapy of the present invention such that it is able to raise or lower (e.g., tune) the amount of energy delivered to a tissue region. In some embodiments, the type of tissue being treated (e.g., liver) is inputted into the software for purposes of allowing the software to regulate (e.g., tune) the delivery of microwave energy to the tissue region based upon pre-calibrated methods for that particular type of tissue region. In other embodiments, the software provides a chart or diagram based upon a particular type of tissue region displaying characteristics useful to a user of the system. In some embodiments, the software provides energy delivering algorithms for purposes of, for example, slowly ramping power to avoid tissue cracking due to rapid out-gassing created by high temperatures. In some embodiments, the software allows a user to choose power, duration of treatment, different treatment algorithms for different tissue types, simultaneous application of power to the antennas in multiple antenna mode, switched power delivery between antennas, coherent and incoherent phasing, etc.

In some embodiments, the software is configured for imaging equipment (e.g., CT, MRI, ultrasound). In some embodiments, the imaging equipment software allows a user to make predictions based upon known thermodynamic and electrical properties of tissue and location of the antenna(s). In some embodiments, the imaging software allows the generation of a three-dimensional map of the location of a tissue region (e.g., tumor, arrhythmia), location of the antenna(s), and to generate a predicted map of the ablation zone.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the following claims.

We claim:

1. A system comprising:
   one or more devices configured for delivery of energy to a tissue; and
   one or more of a power generator, a temperature monitoring device, a power distributor, a coolant source, and a processor;
   wherein said one or more devices configured for delivery of energy to the tissue is
   a device comprising a feedline portion comprising an inner and outer conductor separated by dielectric material, and an antenna portion distal to said feedline portion,
   wherein said feedline portion has an outer diameter that is equal to or less than a 16-gauge needle and wherein said feedline portion comprises one or more coolant pathways between said inner conductor and said outer conductor,
   wherein the feedline portion has a proximal end and a distal end,
   wherein the antenna portion has a proximal end and a distal end,
   wherein said one or more coolant pathways are created by removing a portion of said dielectric material, wherein said one or more coolant pathways are non-linear along the feedline portion, wherein the one or more coolant pathways are non-linear with respect to a feedline portion axis from the proximal end of the feedline portion to the distal end of the feedline portion,
   wherein the inner conductor extends from the proximal end of the feedline portion to the distal end of the antenna portion,
   wherein the outer conductor and dielectric material extend from the proximal end of the feedline portion to the distal end of the feedline portion,
   wherein said outer diameter is equal to or less than a 20-gauge needle, wherein said one or more coolant pathways terminate within said feedline portion;

wherein said feedline portion comprises a triaxial configuration having said inner conductor, said outer conductor, and a middle conductor disposed between the inner and outer conductors.

2. The system of claim 1, wherein said energy is microwave energy.

3. The system of claim 1, wherein said one or more coolant pathways comprise one or more tubes inserted within said feedline portion, wherein said one or more tubes are deformable tubes.

4. The system of claim 1, wherein said middle conductor comprises a metal foil or plating; and/or wherein said middle conductor is less than 1 mm thick.

5. The system of claim 1, wherein said antenna portion is not configured for contact with coolant from the one or more coolant pathways.

6. The system of claim 1, further comprising a tip at said distal end of said antenna portion.

7. The system of claim 1, wherein said one or more coolant pathways is configured such that, when coolant is present in said one or more coolant pathways, the coolant alters a characteristic impedance of the device as compared to the device in an absence of the coolant.

8. The system of claim 1, wherein said one or more coolant pathways comprises two or more coolant pathways; wherein said device is configured to transfer a coolant in a first direction through a first of said two or more coolant pathways and in a second direction through a second of said two or more coolant pathways.

9. The system of claim 1, wherein said one or more coolant pathway channels is configured to achieve cooling with gas coolants via a Joule-Thompson effect.

10. The system of claim 1, wherein said one or more coolant pathways is configured to distribute liquid or gas, wherein said liquid or said gas is provided at its respective critical point temperature.

11. The system of claim 1, wherein said dielectric material is solid, wherein portions of said inner conductor are connected with portions of said outer conductor via said solid dielectric material, wherein said one or more coolant pathways include regions where portions of said inner conductor and portions of said outer conductor are not connected via said solid dielectric material.

12. A method of treating a tissue region, comprising:

a) providing the system of claim 1;

b) positioning the device in a vicinity of a tissue region, and c) delivering an amount of energy with said device to said tissue region.

13. The method of claim 12, wherein said tissue region is a tumor.

14. The method of claim 12, further comprising the step of passing a fluid through said one or more coolant pathways.

15. The method of claim 14, wherein said passing occurs prior to said delivering.

16. The method of claim 14, wherein said passing is conducted under conditions such that a characteristic impedance of said device is altered.

* * * * *